US012390497B2

(12) United States Patent
King et al.

(10) Patent No.: US 12,390,497 B2
(45) Date of Patent: *Aug. 19, 2025

(54) MICROBIAL STRAINS FOR VIRUS INHIBITION

(71) Applicants: MICROBIAL DISCOVERY GROUP, LLC, Franklin, WI (US); UNITED ANIMAL HEALTH, INC., Sheridan, IN (US)

(72) Inventors: Michael R. King, Oak Creek, WI (US); Sona Son, Cudahy, WI (US); Nathan Robert Augspurger, Noblesville, IN (US); Joel Dean Spencer, Westfield, IN (US); Kyle Leistikow, Franklin, WI (US)

(73) Assignees: MICROBIAL DISCOVERY GROUP, LLC, Franklin, WI (US); UNITED ANIMAL HEALTH, INC., Sheridan, IN (US)

( * ) Notice: Subject to any disclaimer, the term of this patent is extended or adjusted under 35 U.S.C. 154(b) by 718 days.

This patent is subject to a terminal disclaimer.

(21) Appl. No.: 17/440,300

(22) PCT Filed: Mar. 19, 2020

(86) PCT No.: PCT/US2020/023586
§ 371 (c)(1),
(2) Date: Sep. 17, 2021

(87) PCT Pub. No.: WO2020/191173
PCT Pub. Date: Sep. 24, 2020

(65) Prior Publication Data
US 2022/0143109 A1    May 12, 2022

Related U.S. Application Data

(60) Provisional application No. 62/820,667, filed on Mar. 19, 2019.

(51) Int. Cl.
| *A61K 35/742* | (2015.01) |
| *A61K 9/00* | (2006.01) |
| *A61K 38/46* | (2006.01) |
| *A61K 38/47* | (2006.01) |
| *A61K 38/48* | (2006.01) |
| *A61P 31/14* | (2006.01) |

(52) U.S. Cl.
CPC .......... *A61K 35/742* (2013.01); *A61K 9/0056* (2013.01); *A61K 38/465* (2013.01); *A61K 38/47* (2013.01); *A61K 38/48* (2013.01); *A61P 31/14* (2018.01)

(58) Field of Classification Search
CPC .. A61K 35/742; A61K 9/0056; A61K 38/465; A61K 38/47; A61K 38/48; A61P 31/14; A61P 31/12; A23K 50/30; A23K 10/16; A23K 10/18; A23K 50/10; A23K 50/75
See application file for complete search history.

(56) References Cited

U.S. PATENT DOCUMENTS

| 11,944,656 B2 * | 4/2024 | King .................. A23K 20/189 |
| 2009/0238907 A1 | 9/2009 | Farmer |
| 2015/0079058 A1 | 3/2015 | Nielsen et al. |
| 2020/0029592 A1 | 1/2020 | King et al. |

FOREIGN PATENT DOCUMENTS

| CN | 101076585 A | 11/2007 |
| CN | 106420841 A | 2/2017 |
| CN | 106714570 A | 5/2017 |
| CN | 109561712 A | 4/2019 |
| CN | 112739358 A | 4/2021 |
| CN | 113164529 A | 7/2021 |
| CN | 113286510 A | 8/2021 |
| WO | 2005019417 A2 | 3/2005 |
| WO | WO2015175667 | 11/2015 |
| WO | 2017151608 A1 | 9/2017 |
| WO | 2019213243 A1 | 11/2019 |
| WO | 2020069255 A1 | 4/2020 |
| WO | 2020072578 A1 | 4/2020 |

OTHER PUBLICATIONS

Machine Translation of CN 106420841 (6 pages, 2024) (Year: 2024).*
Byoung-Joo et al. (Acta Vet Beograd, 2017, 67:153) (Year: 2017).*
Thomas et al. (Animal Feed Sci Technol, 1998, 70:59) (Year: 1998).*
PCT Search Report and Written Opinion prepared for PCT/US2020/023586, May 20, 2020.

(Continued)

*Primary Examiner* — David Steadman
*Assistant Examiner* — Joseph R Spangler
(74) *Attorney, Agent, or Firm* — Barnes & Thornburg LLP

(57) ABSTRACT

The invention relates to compositions comprising microbial strains for use in inhibiting viruses, and methods therefor. More particularly, the invention relates to compositions of isolated *Bacillus* strains selected from the group consisting of isolated *Bacillus* strains 300, 86, 101, 235, 102, 177, A12, 54, 681, 721, strains having all of the identifying characteristics of these strains, and combinations thereof, and methods for use of these strains for virus inhibition.

11 Claims, 16 Drawing Sheets

(56) References Cited

OTHER PUBLICATIONS

Canning, Paisley, et al., "Veterinary Diagnostic and Production Animal Medicine Publications Veterinary Diagnostic and Production Animal Medicine," 2017, Journal of Swine Health and Production, vol. 25, Nr: 3, pp. 129-137.
Peng, Ju-Yi, et al. "Evaluation of Antiviral Activity of Bacillus Licheniformis-Fermented Products Against Porcine Epidemic Diarrhea Virus," 2019, AMB Express, vol. 9, No. 191, pp. 1-12.
Search Report for copending CN Application No. 202080037387.1, mailed Dec. 3, 2023.

\* cited by examiner

MICROBIAL STRAINS FOR VIRUS INHIBITION

CROSS-REFERENCE TO RELATED APPLICATIONS

This application is a national stage entry under 35 USC § 371 (b) of PCT International Application No. PCT/US2020/023586, filed Mar. 19, 2020, which claims priority under 35 U.S.C. § 119 (e) to U.S. Provisional Application Ser. No. 62/820,667 filed on Mar. 19, 2019, the entire disclosure of which is incorporated herein by reference.

FIELD OF THE DISCLOSURE

The invention relates to compositions comprising microbial strains for use in inhibiting viruses, and methods therefor. More particularly, the invention relates to compositions of isolated *Bacillus* strains selected from the group consisting of isolated *Bacillus* strains 300, 86, 101, 235, 102, 177, A12, 54, 681, 721, strains having all of the identifying characteristics of these strains, and combinations thereof, and methods for use of these strains for virus inhibition.

BACKGROUND AND SUMMARY OF THE INVENTION

Effective control of viral infection in animals has remained an unachieved goal, in part, due to high variability in virus replication strategies, readily mutating genomes, and the limited availability of anti-viral drugs. Biologically active peptides act in synergy with other defense mechanisms in both plants and animals and can be considered one of the first forms of protection eukaryotic cells have against viruses. Chemical antiviral agents typically have narrow specificity. Therefore, an alternative antiviral strategy associated with the use of microbial enzymes, which are less toxic and more readily decomposed without accumulation of harmful substances, is needed.

Applicant has developed such an alternative antiviral strategy associated with the use of direct-fed microbial compositions comprising isolated *Bacillus* strains, producing microbial enzymes, wherein the isolated *Bacillus* strains are selected from the group consisting of isolated *Bacillus* strains 300, 86, 101, 235, 102, 177, A12, 54, 681, 721, strains having all of the identifying characteristics of these strains, and combinations thereof.

In one embodiment, a method of feeding an animal is provided. The method comprises the step of administering to the animal a feed composition or drinking water comprising an effective amount of an additive comprising an isolated *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No. B-67219), *Bacillus* strain 86 (NRRL No. B-50944), *Bacillus* strain 102 (NRRL No. B-67276), and *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain causes virus inhibition in the animal.

In another embodiment, a method of controlling a detrimental effect of a virus in an animal is provided. The method comprises the step of administering to the animal a feed composition or drinking water comprising an effective amount of an additive comprising an isolated *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No. B-67219), *Bacillus* strain 86 (NRRL No. B-50944), *Bacillus* strain 102 (NRRL No. B-67276), *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof.

In yet another embodiment, a method of feeding an animal is provided. The method comprises the step of administering to the animal a feed composition or drinking water comprising an effective amount of an additive comprising an isolated *Bacillus* strain, or combinations thereof, wherein the *Bacillus* strain causes virus inhibition in the animal.

In still another embodiment, a method of controlling a detrimental effect of a virus is provided. The method comprises the steps of administering to an animal a feed composition or drinking water comprising an effective amount of an additive comprising an isolated *Bacillus* strain, or combinations thereof, and controlling the detrimental effect of the virus.

In another illustrative aspect, a commercial package is provided comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

In another illustrative embodiment, a feed additive for an animal feed is provided comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

In another embodiment, an additive for the drinking water of an animal is provided comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

In another aspect, an animal feed composition is provided comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

In yet another embodiment, a commercial package is provided comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

In still another embodiment, a feed additive for an animal feed is provided comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

In another illustrative embodiment, an additive for the drinking water of an animal is provided comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

In another aspect, an animal feed composition is provided comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

The various embodiments described in the numbered clauses below are applicable to any of the embodiments described in this "SUMMARY" section and the sections of the patent application titled "DETAILED DESCRIPTION OF ILLUSTRATIVE EMBODIMENTS" or "EXAMPLES" or in the "CLAIMS" appended to this application:

1. A method of feeding an animal, the method comprising the step of administering to the animal a feed composition or drinking water comprising an effective amount of an additive comprising an isolated *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No.

B-67219), *Bacillus* strain 86 (NRRL No. B-50944), *Bacillus* strain 102 (NRRL No. B-67276), and *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain causes virus inhibition in the animal.
2. A method of controlling a detrimental effect of a virus in an animal, the method comprising the step of administering to the animal a feed composition or drinking water comprising an effective amount of an additive comprising an isolated *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No. B-67219), *Bacillus* strain 86 (NRRL No. B-50944), *Bacillus* strain 102 (NRRL No. B-67276), *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof.
3. A method of feeding an animal, the method comprising the step of administering to the animal a feed composition or drinking water comprising an effective amount of an additive comprising an isolated *Bacillus* strain, or combinations thereof, wherein the *Bacillus* strain causes virus inhibition in the animal.
4. A method of controlling a detrimental effect of a virus in an animal, the method comprising the steps of administering to an animal a feed composition or drinking water comprising an effective amount of an additive comprising an isolated *Bacillus* strain, or combinations thereof, and controlling the detrimental effect of the virus in the animal.
5. The method of any one of clauses 1 to 4 wherein the animal is selected from the group consisting of a poultry species, a porcine species, a caprine species, a bovine species, an ovine species, an equine species, and a companion animal.
6. The method of clause 5 wherein the animal is a porcine species and the porcine species is selected from the group consisting of a grow finish pig, a nursery pig, a sow, and a breeding stock pig.
7. The method of clause 6 wherein the animal is a sow.
8. The method of clause 6 wherein the animal is a nursery pig.
9. The method of any one of clauses 1 to 8 wherein the virus is a Rotavirus.
10. The method clause 9 wherein the Rotavirus is Rotavirus A or Rotavirus C.
11. The method of any one of clauses 1 to 8 wherein the virus is a respiratory virus.
12. The method of clause 11 wherein the virus is a porcine reproductive and respiratory syndrome virus.
13. The method of any one of clauses 1 to 12 wherein the *Bacillus* strain produces an enzyme selected from the group consisting of an α-galactosidase, a protease, a lipase, an amylase, a xylanase, a cellulase, and combinations thereof.
14. The method of any one of clauses 1 to 13 further comprising the step of administering to the animal another bacterial strain selected from the group consisting of another *Bacillus* strain, a lactic acid bacterial strain, and combinations thereof.
15. The method of any one of clauses 1 to 14 wherein the strain administered is *Bacillus* strain 300 (NRRL No. B-50943), or a strain having all of the identifying characteristics of *Bacillus* strain 300 (NRRL No. B-50943), in combination with a *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 101 (NRRL No. B-67218), *Bacillus* strain 235 (NRRL No. B-67219), *Bacillus* strain 102 (NRRL No. B-67276), *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 102 (NRRL No. B-67276), a strain having all of the identifying characteristics of *Bacillus* strain 177 (NRRL No. B-67275), or combinations thereof.
16. The method of any one of clauses 1 to 14 wherein the strain administered is *Bacillus* strain 86 (NRRL No. B-50944), or a strain having all of the identifying characteristics of *Bacillus* strain 86 (NRRL No. B-50944), in combination with a *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 101 (NRRL No. B-67218), *Bacillus* strain 235 (NRRL No. B-67219), *Bacillus* strain 102 (NRRL No. B-67276), *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 102 (NRRL No. B-67276), a strain having all of the identifying characteristics of *Bacillus* strain 177 (NRRL No. B-67275), and combinations thereof.

17. The method of any one of clauses 1 to 14 wherein the strains administered are *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

18. The method of any one of clauses 1 to 14 wherein the strains administered are *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

19. The method of any one of clauses 1 to 14 wherein the strain administered is *Bacillus* strain A12 (NRRL No. B67516) or a strain having all of the identifying characteristics of *Bacillus* strain A12 (NRRL No. B67516).

20. The method of any one of clauses 1 to 14 wherein the strain administered is *Bacillus* strain 54 (NRRL No. B67517) or a strain having all of the identifying characteristics of *Bacillus* strain 54 (NRRL No. B67517).

21. The method of any one of clauses 1 to 14 wherein the strain administered is *Bacillus* strain 681 (NRRL No. B67515) or a strain having all of the identifying characteristics of *Bacillus* strain 681 (NRRL No. B67515).

22. The method of any one of clauses 1 to 14 wherein the strain administered is *Bacillus* strain 721 (NRRL No. B67514) or a strain having all of the identifying characteristics of *Bacillus* strain 721 (NRRL No. B67514).

23. The method of any one of clauses 1 to 14 wherein the strain administered is *Bacillus* strain 300 (NRRL No. B-50943) or a strain having all of the identifying characteristics of *Bacillus* strain 300 (NRRL No. B-50943).

24. The method of any one of clauses 1 to 14 wherein the strain administered is *Bacillus* strain 101 (NRRL No. B-67218) or a strain having all of the identifying characteristics of *Bacillus* strain 101 (NRRL No. B-67218).

25. The method of any one of clauses 1 to 14 wherein the strain administered is *Bacillus* strain 235 (NRRL No. B-67219) or a strain having all of the identifying characteristics of *Bacillus* strain 235 (NRRL No. B-67219).

26. The method of any one of clauses 1 to 14 wherein the strain administered is *Bacillus* strain 86 (NRRL No. B-50944) or a strain having all of the identifying characteristics of *Bacillus* strain 86 (NRRL No. B-50944).

27. The method of any one of clauses 1 to 14 wherein the strain administered is *Bacillus* strain 102 (NRRL No. B-67276) or a strain having all of the identifying characteristics of *Bacillus* strain 102 (NRRL No. B-67276).

28. The method of any one of clauses 1 to 14 wherein the strain administered is *Bacillus* strain 177 (NRRL No. B-67275) or a strain having all of the identifying characteristics of *Bacillus* strain 177 (NRRL No. B-67275).

29. The method of any one of clauses 1 to 14 wherein the strain administered is *Bacillus* strain A12 (NRRL No. B67516).

30. The method of any one of clauses 1 to 14 wherein the strain administered is *Bacillus* strain 54 (NRRL No. B67517).

31. The method of any one of clauses 1 to 14 wherein the strain administered is *Bacillus* strain 681 (NRRL No. B67515).

32. The method of any one of clauses 1 to 14 wherein the strain administered is *Bacillus* strain 721 (NRRL No. B67514).

33. The method of any one of clauses 1 to 14 wherein the strain administered is *Bacillus* strain 300 (NRRL No. B-50943).

34. The method of any one of clauses 1 to 14 wherein the strain administered is *Bacillus* strain 101 (NRRL No. B-67218).

35. The method of any one of clauses 1 to 14 wherein the strain administered is *Bacillus* strain 235 (NRRL No. B-67219).

36. The method of any one of clauses 1 to 14 wherein the strain administered is *Bacillus* strain 86 (NRRL No. B-50944).

37. The method of any one of clauses 1 to 14 wherein the strain administered is *Bacillus* strain 102 (NRRL No. B-67276).

38. The method of any one of clauses 1 to 14 wherein the strain administered is *Bacillus* strain 177 ((NRRL No. B-67275).

39. The method of any one of clauses 1 to 38 wherein the *Bacillus* strain is administered in the feed composition at a dose of about $1.0 \times 10^3$ CFU/gram of the feed composition to about $5.0 \times 10^{12}$ CFU/gram of the feed composition.
40. The method of any one of clauses 1 to 38 wherein the *Bacillus* strain is administered in the feed composition at a dose of about $1.0 \times 10^3$ CFU/gram of the feed composition to about $1.0 \times 10^7$ CFU/gram of the feed composition.
41. The method of any one of clauses 1 to 38 wherein the *Bacillus* strain is administered in the feed composition at a dose greater than about $7.0 \times 10^4$ CFU/gram of the feed composition.
42. The method of any one of clauses 1 to 41 further comprising the step of administering an antibiotic to the animal.
43. The method of any one of clauses 1 to 42 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.
44. The method of clause 43 wherein the enzyme is an NSPase or a phytase.
45. The method of any one of clauses 1 to 7 or 9 to 44 wherein the animal is a sow and the *Bacillus* strain is administered during lactation.
46. The method of any one of clauses 1 to 7 or 9 to 44 wherein the animal is a sow and the *Bacillus* strain is administered during gestation.
47. The method of any one of clauses 1 to 46 wherein the feed composition is administered daily to the animal.
48. The method of clause 1 wherein the animal is selected from the group consisting of a chicken, a pig, a horse, a pony, a cow, a turkey, a goat, a sheep, a quail, a pheasant, an ostrich, a duck, a fish, and a crustacean.
49. The method of any one of clauses 1 to 48 wherein the virus inhibition or controlling the detrimental effect of the virus comprises reducing the number of viruses in the animal or reducing viral disease symptoms in the animal.
50. The method of clause 9 or 10 wherein the virus inhibition or controlling the detrimental effect of the virus in the animal comprises reducing enteric disease in the animal.
51. The method of clause 11 or 12 wherein the virus inhibition or controlling the detrimental effect of the virus in the animal comprises reducing pneumonia in the animal.
52. The method of any one of clauses 1 to 51 further comprising reducing *E. coli* virulence genes in the animal.
53. The method of any one of clauses 1 to 51 further comprising reducing *Salmonella* disease in the animal.
54. The method of clause 53 wherein the *Salmonella* disease is caused by *Salmonella choleraesuis*.
55. A commercial package comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).
56. A feed additive for an animal feed comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).
57. An additive for the drinking water of an animal comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).
58. An animal feed composition comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).
59. A commercial package comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101

(NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

60. A feed additive for an animal feed comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

61. An additive for the drinking water of an animal comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

62. An animal feed composition comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

63. The commercial package, feed additive, feed composition, or additive for the drinking water of the animal of any one of clauses 55 to 62 wherein the *Bacillus* strain causes virus inhibition in an animal.

64. The feed additive or additive for the drinking water of the animal of clause 56, 57, 60, or 61 in the form of a concentrate.

65. The feed additive or additive for the drinking water of the animal of clause 56, 57, 60, or 61 in the form of a superconcentrate.

66. The feed additive, feed composition, or additive for the drinking water of the animal of any one of clauses 56 to 58 or 60 to 62 in dry form.

67. The feed composition of clause 66 in pelleted form.

68. The commercial package of clause 55 or 59 wherein the strains are in a form selected from the group consisting of a powder, a liquid, and a pellet form.

69. The commercial package, feed additive, additive for the drinking water of the animal, or feed composition of any one of clauses 55 to 68 further comprising a carrier for the *Bacillus* strains.

70. The commercial package, feed additive, additive for the drinking water of the animal, or feed composition of clause 69 wherein the carrier is selected from the group consisting of a bran, rice hulls, a salt, a dextrin, and combinations thereof.

71. The commercial package, feed additive, additive for the drinking water of the animal, or feed composition of any one of clauses 55 to 70 in a bag.

72. The commercial package, feed additive, additive for the drinking water of the animal, or feed composition of clause 71 wherein the bag is a plastic bag or a paper bag.

73. The commercial package, feed additive, additive for the drinking water of the animal, or feed composition of any one of clauses 55 to 72 further comprising instructions for use of one or more of the *Bacillus* strains.

74. The commercial package, feed additive, feed composition, or additive for the drinking water of the animal of any one of clauses 71 to 73 in a 20-pound bag.

75. The commercial package, feed additive, feed composition, or additive for the drinking water of the animal of any one of clauses 71 to 73 in a 50-pound bag.

76. The feed additive or additive for the drinking water of the animal of any one of clauses 56, 57, 60, 61, 63 to 66, or 67 to 75 in powder form.

77. The feed additive or additive for the drinking water of the animal of any one of clauses 56, 57, 60, 61 or 63 to 65 in liquid form.

78. The commercial package, feed additive, additive for the drinking water of the animal, or feed composition of any one of clauses 55 to 77 in a container for commercial use.

79. The commercial package, feed additive, additive for the drinking water of the animal, or feed composition of clause 78 wherein the container comprises plastic.

80. The commercial package, feed additive, additive for the drinking water of the animal, or feed composition of clause 78 wherein the container comprises paper.

81. The commercial package, feed additive, additive for the drinking water of the animal, or feed composition of any one of clauses 55 to 80 further comprising a binder.

82. The commercial package, feed additive, additive for the drinking water of the animal, or feed composition of clause 81 wherein the binder is selected from the group consisting of clay, yeast cell wall components, aluminum silicate (HSCAS), and glucan, or combinations thereof.

DETAILED DESCRIPTION OF ILLUSTRATIVE EMBODIMENTS

Figure 1:
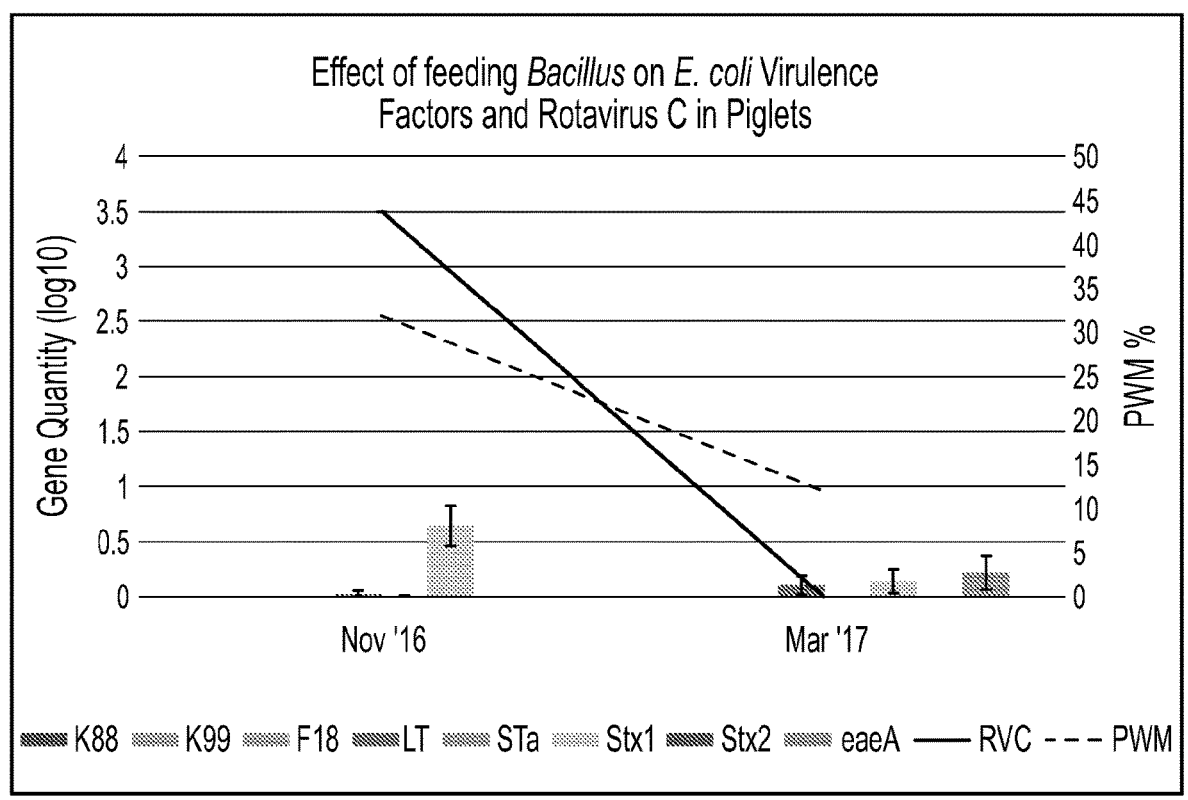
FIG. 1 is a graph showing a gene quantity and pre wean mortality (PWM) comparison between two sampling time points in sow unit A. The bars correspond to the legend left to right in each dated group.

The invention described herein relates to compositions comprising microbial strains for use in inhibiting viruses, and methods therefor. For example, the invention relates to compositions of isolated *Bacillus* strains selected from the group consisting of isolated *Bacillus* strains 300, 86, 101, 235, 102, 177, A12, 54, 681, 721, strains having all of the identifying characteristics of these strains, and combinations thereof, and methods for use of these strains for virus inhibition.

The various embodiments described in the numbered clauses below are applicable to any of the embodiments described in this "DETAILED DESCRIPTION OF ILLUSTRATIVE EMBODIMENTS" section and the sections of the patent application titled "SUMMARY" or "EXAMPLES" or in the "CLAIMS" appended to this application:

1. A method of feeding an animal, the method comprising the step of administering to the animal a feed composition or drinking water comprising an effective amount of an additive comprising an isolated *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No. B-67219), *Bacillus* strain 86 (NRRL No. B-50944), *Bacillus* strain 102 (NRRL No. B-67276), and *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain causes virus inhibition in the animal.

2. A method of controlling a detrimental effect of a virus in an animal, the method comprising the step of administering to the animal a feed composition or drinking water comprising an effective amount of an additive comprising an isolated *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No. B-67219), *Bacillus* strain 86 (NRRL No. B-50944), *Bacillus* strain 102 (NRRL No. B-67276), *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof.

3. A method of feeding an animal, the method comprising the step of administering to the animal a feed composition or drinking water comprising an effective amount of an additive comprising an isolated *Bacillus* strain, or combinations thereof, wherein the *Bacillus* strain causes virus inhibition in the animal.

4. A method of controlling a detrimental effect of a virus, the method comprising the steps of administering to an animal a feed composition or drinking water comprising an effective amount of an additive comprising an isolated *Bacillus* strain, or combinations thereof, and controlling the detrimental effect of the virus.

5. The method of any one of clauses 1 to 4 wherein the animal is selected from the group consisting of a poultry species, a porcine species, a caprine species, a bovine species, an ovine species, an equine species, and a companion animal.

6. The method of clause 5 wherein the animal is a porcine species and the porcine species is selected from the group consisting of a grow finish pig, a nursery pig, a sow, and a breeding stock pig.

7. The method of clause 6 wherein the animal is a sow.

8. The method of clause 6 wherein the animal is a nursery pig.

9. The method of any one of clauses 1 to 8 wherein the virus is a Rotavirus.

10. The method clause 9 wherein the Rotavirus is Rotavirus A or Rotavirus C.

11. The method of any one of clauses 1 to 8 wherein the virus is a respiratory virus.

12. The method of clause 11 wherein the virus is a porcine reproductive and respiratory syndrome virus.

13. The method of any one of clauses 1 to 12 wherein the *Bacillus* strain produces an enzyme selected from the group consisting of an α-galactosidase, a protease, a lipase, an amylase, a xylanase, a cellulase, and combinations thereof.

14. The method of any one of clauses 1 to 13 further comprising the step of administering to the animal another bacterial strain selected from the group consisting of another *Bacillus* strain, a lactic acid bacterial strain, and combinations thereof.

15. The method of any one of clauses 1 to 14 wherein the strain administered is *Bacillus* strain 300 (NRRL No. B-50943), or a strain having all of the identifying characteristics of *Bacillus* strain 300 (NRRL No. B-50943), in combination with a *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 101 (NRRL No. B-67218), *Bacillus* strain 235 (NRRL No. B-67219), *Bacillus* strain 102 (NRRL No. B-67276), *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 102 (NRRL No. B-67276), a strain having all of the identifying characteristics of *Bacillus* strain 177 (NRRL No. B-67275), or combinations thereof.

16. The method of any one of clauses 1 to 14 wherein the strain administered is *Bacillus* strain 86 (NRRL No. B-50944), or a strain having all of the identifying characteristics of *Bacillus* strain 86 (NRRL No. B-50944), in combination with a *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 101 (NRRL No. B-67218), *Bacillus* strain 235 (NRRL No. B-67219), *Bacillus* strain 102 (NRRL No. B-67276), *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 102 (NRRL No. B-67276), a strain having all of the identifying characteristics of *Bacillus* strain 177 (NRRL No. B-67275), and combinations thereof.

17. The method of any one of clauses 1 to 14 wherein the strains administered are *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

18. The method of any one of clauses 1 to 14 wherein the strains administered are *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

19. The method of any one of clauses 1 to 14 wherein the strain administered is *Bacillus* strain A12 (NRRL No. B67516) or a strain having all of the identifying characteristics of *Bacillus* strain A12 (NRRL No. B67516).

20. The method of any one of clauses 1 to 14 wherein the strain administered is *Bacillus* strain 54 (NRRL No. B67517) or a strain having all of the identifying characteristics of *Bacillus* strain 54 (NRRL No. B67517).

21. The method of any one of clauses 1 to 14 wherein the strain administered is *Bacillus* strain 681 (NRRL No.

B67515) or a strain having all of the identifying characteristics of *Bacillus* strain 681 (NRRL No. B67515).

22. The method of any one of clauses 1 to 14 wherein the strain administered is *Bacillus* strain 721 (NRRL No. B67514) or a strain having all of the identifying characteristics of *Bacillus* strain 721 (NRRL No. B67514).

23. The method of any one of clauses 1 to 14 wherein the strain administered is *Bacillus* strain 300 (NRRL No. B-50943) or a strain having all of the identifying characteristics of *Bacillus* strain 300 (NRRL No. B-50943).

24. The method of any one of clauses 1 to 14 wherein the strain administered is *Bacillus* strain 101 (NRRL No. B-67218) or a strain having all of the identifying characteristics of *Bacillus* strain 101 (NRRL No. B-67218).

25. The method of any one of clauses 1 to 14 wherein the strain administered is *Bacillus* strain 235 (NRRL No. B-67219) or a strain having all of the identifying characteristics of *Bacillus* strain 235 (NRRL No. B-67219).

26. The method of any one of clauses 1 to 14 wherein the strain administered is *Bacillus* strain 86 (NRRL No. B-50944) or a strain having all of the identifying characteristics of *Bacillus* strain 86 (NRRL No. B-50944).

27. The method of any one of clauses 1 to 14 wherein the strain administered is *Bacillus* strain 102 (NRRL No. B-67276) or a strain having all of the identifying characteristics of *Bacillus* strain 102 (NRRL No. B-67276).

28. The method of any one of clauses 1 to 14 wherein the strain administered is *Bacillus* strain 177 (NRRL No. B-67275) or a strain having all of the identifying characteristics of *Bacillus* strain 177 (NRRL No. B-67275).

29. The method of any one of clauses 1 to 14 wherein the strain administered is *Bacillus* strain A12 (NRRL No. B67516).

30. The method of any one of clauses 1 to 14 wherein the strain administered is *Bacillus* strain 54 (NRRL No. B67517).

31. The method of any one of clauses 1 to 14 wherein the strain administered is *Bacillus* strain 681 (NRRL No. B67515).

32. The method of any one of clauses 1 to 14 wherein the strain administered is *Bacillus* strain 721 (NRRL No. B67514).

33. The method of any one of clauses 1 to 14 wherein the strain administered is *Bacillus* strain 300 (NRRL No. B-50943).

34. The method of any one of clauses 1 to 14 wherein the strain administered is *Bacillus* strain 101 (NRRL No. B-67218).

35. The method of any one of clauses 1 to 14 wherein the strain administered is *Bacillus* strain 235 (NRRL No. B-67219).

36. The method of any one of clauses 1 to 14 wherein the strain administered is *Bacillus* strain 86 (NRRL No. B-50944).

37. The method of any one of clauses 1 to 14 wherein the strain administered is *Bacillus* strain 102 (NRRL No. B-67276).

38. The method of any one of clauses 1 to 14 wherein the strain administered is *Bacillus* strain 177 ((NRRL No. B-67275).

39. The method of any one of clauses 1 to 38 wherein the *Bacillus* strain is administered in the feed composition at a dose of about $1.0 \times 10^3$ CFU/gram of the feed composition to about $5.0 \times 10^{12}$ CFU/gram of the feed composition.

40. The method of any one of clauses 1 to 38 wherein the *Bacillus* strain is administered in the feed composition at a dose of about $1.0 \times 10^3$ CFU/gram of the feed composition to about $1.0 \times 10^7$ CFU/gram of the feed composition.

41. The method of any one of clauses 1 to 38 wherein the *Bacillus* strain is administered in the feed composition at a dose greater than about $7.0 \times 10^4$ CFU/gram of the feed composition.

42. The method of any one of clauses 1 to 41 further comprising the step of administering an antibiotic to the animal.

43. The method of any one of clauses 1 to 42 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

44. The method of clause 43 wherein the enzyme is an NSPase or a phytase.

45. The method of any one of clauses 1 to 7 or 9 to 44 wherein the animal is a sow and the *Bacillus* strain is administered during lactation.

46. The method of any one of clauses 1 to 7 or 9 to 44 wherein the animal is a sow and the *Bacillus* strain is administered during gestation.

47. The method of any one of clauses 1 to 46 wherein the feed composition is administered daily to the animal.

48. The method of clause 1 wherein the animal is selected from the group consisting of a chicken, a pig, a horse, a pony, a cow, a turkey, a goat, a sheep, a quail, a pheasant, an ostrich, a duck, a fish, and a crustacean.

49. The method of any one of clauses 1 to 48 wherein the virus inhibition or controlling the detrimental effect of the virus comprises reducing the number of viruses in the animal or reducing viral disease symptoms in the animal.

50. The method of clause 9 or 10 wherein the virus inhibition or controlling the detrimental effect of the virus in the animal comprises reducing enteric disease in the animal.

51. The method of clause 11 or 12 wherein the virus inhibition or controlling the detrimental effect of the virus in the animal comprises reducing pneumonia in the animal.

52. The method of any one of clauses 1 to 51 further comprising reducing *E. coli* virulence genes in the animal.

53. The method of any one of clauses 1 to 51 further comprising reducing *Salmonella* disease in the animal.

54. The method of clause 53 wherein the *Salmonella* disease is caused by *Salmonella choleraesuis*.

55. A commercial package comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

56. A feed additive for an animal feed comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

57. An additive for the drinking water of an animal comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

58. An animal feed composition comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

59. A commercial package comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

60. A feed additive for an animal feed comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

61. An additive for the drinking water of an animal comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

62. An animal feed composition comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

63. The commercial package, feed additive, feed composition, or additive for the drinking water of the animal of any one of clauses 55 to 62 wherein the *Bacillus* strain causes virus inhibition in an animal.

64. The feed additive or additive for the drinking water of the animal of clause 56, 57, 60, or 61 in the form of a concentrate.

65. The feed additive or additive for the drinking water of the animal of clause 56, 57, 60, or 61 in the form of a superconcentrate.

66. The feed additive, feed composition, or additive for the drinking water of the animal of any one of clauses 56 to 58 or 60 to 62 in dry form.

67. The feed composition of clause 66 in pelleted form.

68. The commercial package of clause 55 or 59 wherein the strains are in a form selected from the group consisting of a powder, a liquid, and a pellet form.

69. The commercial package, feed additive, additive for the drinking water of the animal, or feed composition of any one of clauses 55 to 68 further comprising a carrier for the *Bacillus* strains.

70. The commercial package, feed additive, additive for the drinking water of the animal, or feed composition of clause 69 wherein the carrier is selected from the group consisting of a bran, rice hulls, a salt, a dextrin, and combinations thereof.

71. The commercial package, feed additive, additive for the drinking water of the animal, or feed composition of any one of clauses 55 to 70 in a bag.

72. The commercial package, feed additive, additive for the drinking water of the animal, or feed composition of clause 71 wherein the bag is a plastic bag or a paper bag.

73. The commercial package, feed additive, additive for the drinking water of the animal, or feed composition of any one of clauses 55 to 72 further comprising instructions for use of one or more of the *Bacillus* strains.

74. The commercial package, feed additive, feed composition, or additive for the drinking water of the animal of any one of clauses 71 to 73 in a 20-pound bag.

75. The commercial package, feed additive, feed composition, or additive for the drinking water of the animal of any one of clauses 71 to 73 in a 50-pound bag.

76. The feed additive or additive for the drinking water of the animal of any one of clauses 56, 57, 60, 61, 63 to 66, or 67 to 75 in powder form.

77. The feed additive or additive for the drinking water of the animal of any one of clauses 56, 57, 60, 61 or 63 to 65 in liquid form.

78. The commercial package, feed additive, additive for the drinking water of the animal, or feed composition of any one of clauses 55 to 77 in a container for commercial use.

79. The commercial package, feed additive, additive for the drinking water of the animal, or feed composition of clause 78 wherein the container comprises plastic.

80. The commercial package, feed additive, additive for the drinking water of the animal, or feed composition of clause 78 wherein the container comprises paper.

81. The commercial package, feed additive, additive for the drinking water of the animal, or feed composition of any one of clauses 55 to 80 further comprising a binder.

82. The commercial package, feed additive, additive for the drinking water of the animal, or feed composition of clause 81 wherein the binder is selected from the group consisting of clay, yeast cell wall components, aluminum silicate (HSCAS), and glucan, or combinations thereof.

In various embodiments, the animal to which a feed additive, a feed composition, or drinking water as described herein is administered can be selected from the group consisting of a poultry species, a porcine species, a caprine species, a bovine species, an ovine species, an equine species, and a companion animal. In the embodiment where the animal is a companion animal, the companion animal can be, for example, a canine species or a feline species. In the embodiment where the animal is a porcine species, the porcine species can be selected from the group consisting of a grow finish pig, a nursery pig, a sow, and a breeding stock pig. In various exemplary embodiments, the animal can be selected from the group consisting of a chicken (e.g., a broiler or a layer), a pig, a horse, a pony, a cow, a turkey, a goat, a sheep, a quail, a pheasant, an ostrich, a duck, a fish (e.g., a tilapia, a catfish, a flounder, or a salmon), or a crustacean (e.g., a shrimp or a crab). In yet another embodiment, the animal is a sow or a nursery pig, or the progeny of a sow fed any of the *Bacillus* strains described herein. In another embodiment, the feed additive, feed composition, or drinking water as described herein could be administered to a human.

In various embodiments of the method, commercial package, feed additive, feed composition, or additive for drinking water described herein, the *Bacillus* strain can have an effect selected from the group consisting of causing virus inhibition in the animal or controlling a detrimental effect of a virus wherein virus "inhibition" or "controlling a detrimental effect" of a virus can mean reducing the number of viruses or viral genes in the animal, controlling or reducing viral replication in the animal, preventing or reducing viral disease in the animal, or preventing or reducing any of the symptoms of viral disease in the animal, or a combination thereof. In another aspect, the virus inhibition or controlling the detrimental effect of the virus in the animal can comprise, for example, reducing or preventing enteric disease in the animal or reducing or preventing pneumonia (e.g., bronchopneumonia) in the animal or reducing or preventing pre-wean mortality in the animal, or reducing or preventing peritonitis in the animal, or combinations thereof. In another embodiment of the method, commercial package, feed additive, feed composition, or additive for drinking water described herein, *E. coli* virulence genes can be reduced in the animal, or *Salmonella* disease can be reduced in the animal, for example, *Salmonella* disease caused by *Salmonella choleraesuis*, as a result of feeding the animal the *Bacillus* strain.

In any of the embodiments described herein the virus can be a Rotavirus, such as Rotavirus A or Rotavirus C. In another embodiment, the virus can be a respiratory virus, such as a porcine reproductive and respiratory syndrome virus. In yet other embodiments, the virus can be a single-stranded (+strand or "sense") DNA virus, a double-stranded DNA virus, a double-stranded RNA virus, a single-stranded (+strand or "sense") RNA virus, a single-stranded (−strand or "antisense") RNA virus, a single-stranded (+strand or "sense") RNA-RT virus with a DNA intermediate in its life-cycle, or a double-stranded DNA-RT virus with an RNA intermediate in its life-cycle. In other embodiments, the virus can be any virus that infects an animal and causes viral disease in the animal.

In any of the embodiments, described herein the *Bacillus* strain can be a *Bacillus subtilis* strain (e.g., strains 86, 300, 101, 235, A12, 681, 721, and 54), or a *Bacillus pumilus* strain (e.g., strains 102 and 177).

In any embodiments described herein, the *Bacillus* strains can be administered alone or in any combination, or can be in the form of any composition described herein so that the strains are alone or in any combination in the compositions described herein. The *Bacillus* strains described herein can also be used in combination with other microbial strains, including other *Bacillus* strains or *Lactobacillus* strains. Exemplary combinations include *Bacillus* strains A12, 54, 681, and 721 (described herein) in any combination with any combination of *Bacillus* strains 86, 300, 101, 102, 177, and 235, described in U.S. Appl. Publication No. U.S. 2017/0079308 and U.S. Appl. Publication No. U.S. 2017/0246224, each incorporated herein by reference. Another exemplary combination includes *Bacillus* strains A12, 54, 681, 721, 86, and 300 in any combination. Another exemplary combination includes *Bacillus* strains 86, 300, 101, 102, 177, and 235 in any combination. Another exemplary combination includes *Bacillus* strain 300 in combination with any of strains 86, 101, 102, 177, 235, A12, 54, 681, and 721, in any combination. Another exemplary combination includes *Bacillus* strain 86 in combination with any of strains 300, 101, 102, 177, 235, A12, 54, 681, and 721, in any combination.

In one embodiment, a method of feeding an animal is provided. The method comprises the step of administering to the animal a feed composition or drinking water comprising an effective amount of an additive comprising an isolated *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No. B-67219), *Bacillus* strain 86 (NRRL No. B-50944), *Bacillus* strain 102 (NRRL No. B-67276), and *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof, wherein the *Bacillus* strain causes virus inhibition in the animal.

In another embodiment, a method of controlling a detrimental effect of a virus in an animal is provided. The method comprises the step of administering to the animal a feed composition or drinking water comprising an effective amount of an additive comprising an isolated *Bacillus* strain selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No. B-67219), *Bacillus* strain 86 (NRRL No. B-50944), *Bacillus* strain 102 (NRRL No. B-67276), *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of *Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof.

In yet another embodiment, a method of feeding an animal is provided. The method comprises the step of administering to the animal a feed composition or drinking water comprising an effective amount of an additive comprising an isolated *Bacillus* strain, or combinations thereof, wherein the *Bacillus* strain causes virus inhibition in the animal.

In another aspect, a method of controlling a detrimental effect of a virus is provided. The method comprises the steps of administering to an animal a feed composition or drinking water comprising an effective amount of an additive comprising an isolated *Bacillus* strain, or combinations thereof, and controlling the detrimental effect of the virus.

In one embodiment of the invention, an effective amount of the *Bacillus* strain can be administered to cause virus inhibition in the animal. By "effective amount" is meant an amount of the *Bacillus* strain (e.g., strain A12, or 54, or 681, or 721, or 101, or 235, or 300, or 86, or 102, or 177) capable of virus inhibition or capable of controlling a detrimental effect of the virus in the animal by any mechanism.

In embodiments described herein wherein the compositions of the present invention comprising *Bacillus* strains A12, and/or 54, and/or 681, and/or 721, and/or 300, and/or 101, and/or 235, and/or 86, and/or 102, and/or 177, or strains having their identifying characteristics, are administered to an animal, the compositions are preferably administered to animals orally in a feed composition or in drinking water, but any other effective method of administration known to those skilled in the art may be utilized such as in a paste, a liquid drench, a top dress, or a capsule. In one illustrative embodiment, the *Bacillus* strains A12, and/or 54, and/or 681, and/or 721, and/or 300, and/or 101, and/or 235, and/or 86, and/or 102, and/or 177, or strains having their identifying characteristics, are provided in the form of an additive for addition to the drinking water of an animal. In another embodiment, the strains may be used as a litter treatment.

In another illustrative embodiment, the *Bacillus* strains A12, and/or 54, and/or 681, and/or 721, and/or 300, and/or 101, and/or 235, and/or 86, and/or 102, and/or 177, or strains having their identifying characteristics, are provided in the form of a feed additive for addition to a feed composition. The feed composition may contain *Bacillus* strain A12, and/or 54, and/or 681, and/or 721, and/or 300, and/or 101, and/or 235, and/or 86, and/or 102, and/or 177, or strains having their identifying characteristics, in a mixture with an animal feed blend, including any art-recognized animal feed blend or any animal feed blend described herein. As used herein, "feed composition" or "animal feed composition" means a feed composition comprising *Bacillus* strain A12, and/or *Bacillus* strain 54, and/or *Bacillus* strain 682, and/or *Bacillus* strain 721, and/or 300, and/or 101, and/or 235, and/or 86, and/or 102, and/or 177, or strains having their identifying characteristics, in a mixture with an animal feed blend, and, optionally any other components that could be used in a feed composition, including other bacterial strains, such as other *Bacillus* strains or *Lactobacillus* strains. In one embodiment, the feed composition may be in the form of a ground meal.

Any animal feed blend, including those known in the art and those described herein, may be used in accordance with the methods and compositions described in this patent application, such as rapeseed meal, cottonseed meal, soybean meal, cornmeal, barley, wheat, silage, and haylage. In various embodiments, the animal feed blend can be supplemented with *Bacillus* strain A12, and/or *Bacillus* strain 54, and/or *Bacillus* strain 681, and/or *Bacillus* strain 721, and/or 300, and/or 101, and/or 235, and/or 86, and/or 102, and/or 177, or strains having their identifying characteristics, but other ingredients may optionally be added to the animal feed blend, including other bacterial strains, such as other *Bacillus* strains or *Lactobacillus* strains.

In various illustrative embodiments, optional ingredients of the animal feed blend include sugars and complex carbohydrates such as both water-soluble and water-insoluble monosaccharides, disaccharides, and polysaccharides. Other optional ingredients include dried distillers grain solubles, fat (e.g., crude fat), phosphorous, sodium bicarbonate, limestone, salt, phytate, calcium, sodium, sulfur, magnesium, potassium, copper, iron, manganese, zinc, ash, fish oil, an oil derived from fish meal, raw seed (e.g., flaxseed), an antioxidant, and starch. In another embodiment, minerals may be added in the form of a mineral premix.

Optional amino acid ingredients that may be added to the animal feed blend are arginine, histidine, isoleucine, leucine, lysine, cysteine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that may be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. In another embodiment, vitamins may be added in the form of a vitamin premix. In yet another embodiment, protein ingredients may be added to the animal feed blend and include protein obtained from meat meal, bone meal, or fish meal, liquid or powdered egg, fish solubles, crude protein, and the like.

In another illustrative aspect, any medicament ingredients known in the art may be added to the animal feed blend or to an additive for the drinking water of the animal, such as antibiotics. In various embodiments, the antibiotic is selected from the group consisting of ampicillin, chloramphenicol, ciprofloxacin, clindamycin, tetracycline, chlortetracycline, DENAGARD™ (i.e., tiamulin), BMD™ (i.e., bacitracin methylene disalicylate), MECADOX® or CARBADOX™ (i.e., carbadox), STAFAC™ (i.e., virginiamycin), erythromycin, levofloxacin, trimethoprim/sulfamethoxazole, trimethoprim, daptomycin, rifampicin, TYLAN™ (i.e., tylosin), PULMOTIL™ (i.e., tilmicosin), vancomycin, gentamicin, Neomycin, Kavault (Avilamycin), and combinations thereof. In another embodiment, the animal feed blend, the feed composition, the feed additive, or the additive for the drinking water of the animal may contain no antibiotics.

In another illustrative embodiment, one or more enzymes may be added to the animal feed blend. In various embodiments, the enzymes that may be added include a galactosidase, a phytase, a protease, a lipase, an amylase, a hemicellulase, an arabinoxylanase, a xylanase, a cellulase, an NSPase, combinations thereof, and any other enzyme that improves the effectiveness of the feed composition for virus inhibition or controlling a detrimental effect of a virus. In yet another embodiment, yeast, fungi (e.g., *Aspergillus* or *Trichoderma*), or micronutrients may be added to the animal feed. Any of the ingredients described above that are suitable for addition to an additive for the drinking water of the animal may be added as a component of the additive for the drinking water of the animal as described herein.

In various illustrative embodiments, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics), or any other bacterial strains added in addition to *Bacillus* strain A12, and/or 54, and/or 681, and/or 721, and/or 300, and/or 101, and/or 235, and/or 86, and/or 102, and/or 177, or strains having their identifying characteristics, can be administered in the feed composition at a dose of about $1.0 \times 10^3$ CFU/gram of the feed composition to about $5.0 \times 10^{12}$ CFU/gram of the feed composition or at a dose of about $1.0 \times 10^3$ CFU/gram of the feed composition to about $1.0 \times 10^7$ CFU/gram of the feed composition. In other embodiments, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics) is administered in the feed composition at a dose greater than about $1.0 \times 10^3$ CFU/gram of the feed composition, at a dose greater than about $1.1 \times 10^3$ CFU/gram of the feed composition, at a dose greater than about $1.25 \times 10^3$ CFU/gram of the feed composition, at a dose greater than about $1.5 \times 10^3$ CFU/gram of the feed composition, at a dose greater than about $1.75 \times 10^3$ CFU/gram of the feed composition, at a dose greater than about $1.0 \times 10^4$ CFU/gram of the feed composition, at a dose greater than about $2.0 \times 10^4$ CFU/gram of the feed composition, at a dose greater than about $3.0 \times 10^4$ CFU/gram of the feed composition, at a dose greater than about $4.0 \times 10^4$ CFU/gram of the feed composition, at a dose greater than about $5.0 \times 10^4$ CFU/gram of the feed composition, at a dose greater than about $6.0 \times 10^4$ CFU/gram of the feed composition, at a dose greater than about $7.0 \times 10^4$ CFU/gram of the feed composition, at a dose greater than about $8.0 \times 10^4$ CFU/gram of the feed composition, at a dose greater than about $1.0 \times 10^5$ CFU/gram of the feed composition, at a dose greater than about $1.0 \times 10^6$ CFU/gram of the feed composition, at a dose greater than about $1.0 \times 10^7$ CFU/gram of the feed composition, at a dose greater than about $1.0 \times 10^8$ CFU/gram of the feed composition, at a dose greater than about $1.0 \times 10^9$ CFU/gram of the feed composition, at a dose greater than about $1.0 \times 10^{10}$ CFU/gram of the feed composition, at a dose greater than about $1.0 \times 10^{11}$ CFU/gram of the feed composition, or at a dose greater than about $1.0 \times 10^{12}$ CFU/gram of the feed composition. In yet another embodiment, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics) is administered in the feed composition at a dose of about $7.3 \times 10^4$ CFU/gram of the feed composition. In another embodiment, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics), or any other bacterial strains added in addition to *Bacillus* strain A12, and/or 54, and/or 681, and/or 721, and/or 300, and/or 101, and/or 235, and/or 86, and/or 102, and/or 177, or strains having their identifying characteristics, can be administered in the feed composition at a dose of about $1.0 \times 10^2$ CFU/gram of the feed composition to about $5.0 \times 10^{12}$ CFU/gram of the feed composition or at a dose of about $1.0 \times 10^2$ CFU/gram of the feed composition to about $1.0 \times 10^7$ CFU/gram of the feed composition, or at a dose greater than about $1.0 \times 10^2$ CFU/gram of the feed composition. In another embodiment, any of the dosages described herein can be in CFU/ml of drinking water in embodiments where the strains are administered in the drinking water of the animal.

In various embodiments, the *Bacillus* strain (e.g., *Bacillus* strain A12, and/or 54, and/or 681, and/or 721, and/or 300, and/or 101, and/or 235, and/or 86, and/or 102, and/or 177, or strains having their identifying characteristics) for use in accordance with the methods and compositions described herein can be selected from the group consisting of *Bacillus* strain A12 (NRRL No. B67516), *Bacillus* strain 54 (NRRL No. B67517), *Bacillus* strain 681 (NRRL No. B67515), *Bacillus* strain 721 (NRRL No. B67514), *Bacillus* strain 300 (NRRL No. B-50943), *Bacillus* strain 101 (NRRL No. B-67218), *Bacillus* strain 235 (NRRL No. B-67219), *Bacillus* strain 86 (NRRL No. B-50944), *Bacillus* strain 102 (NRRL No. B-67276), and *Bacillus* strain 177 (NRRL No. B-67275), a strain having all of the identifying characteristics of *Bacillus* strain A12 (NRRL No. B67516), a strain having all of the identifying characteristics of *Bacillus* strain 54 (NRRL No. B67517), a strain having all of the identifying characteristics of *Bacillus* strain 681 (NRRL No. B67515), a strain having all of the identifying characteristics of *Bacillus* strain 721 (NRRL No. B67514), a strain having all of the identifying characteristics of *Bacillus* strain 300 (NRRL No. B-50943), a strain having all of the identifying characteristics of *Bacillus* strain 101 (NRRL No. B-67218), a strain having all of the identifying characteristics of

*Bacillus* strain 235 (NRRL No. B-67219), a strain having all of the identifying characteristics of *Bacillus* strain 86 (NRRL No. B-50944), a strain having all of the identifying characteristics of *Bacillus* strain 102 (NRRL No. B-67276), a strain having all of the identifying characteristics of *Bacillus* strain 177 (NRRL No. B-67275), and combinations thereof. *Bacillus* strains A12, 54, 681, and 721 were deposited on Sep. 14, 2017 at the Agricultural Research Service Culture Collection (NRRL), National Center for Agricultural Utilization Research, Agricultural Research Service, USDA, 1815 North University Street, Peoria, Illinois 61604-3999, and were given accession numbers B67516, B67517, B67515, and B67514, respectively. The deposits were made under the provisions of the Budapest Treaty on the International Recognition of the Deposit of Microorganisms for the Purposes of Patent Procedure. The NRRL strain designations are B67516, B67517, B67515, and B67514 which are equivalent to *Bacillus* strain A12, 54, 681, and 721, respectively, as referred to in the application. *Bacillus* strain MDG86 and *Bacillus* strain MDG300 were deposited on Mar. 14, 2014 at the Agricultural Research Service Culture Collection (NRRL), National Center for Agricultural Utilization Research, Agricultural Research Service, USDA, 1815 North University Street, Peoria, Illinois 61604-3999, and were given accession numbers B-50944 and B-50943, respectively. The deposits were made under the provisions of the Budapest Treaty on the International Recognition of the Deposit of Microorganisms for the Purposes of Patent Procedure. The NRRL strain designations are MDG86 and MDG300, which are equivalent to *Bacillus* strain 86 and 300, respectively, as referred to in the application. *Bacillus* strain MDG 101 and *Bacillus* strain MDG 235 were deposited on Jan. 4, 2016 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67218 and B-67219, respectively. *Bacillus* strain MGL177 and *Bacillus* strain MGL102 were deposited on Jun. 7, 2016 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67275 and B-67276, respectively. The deposits were made under the provisions of the Budapest Treaty on the International Recognition of the Deposit of Microorganisms for the Purposes of Patent Procedure. The NRRL strain designations are MDG 101, MDG 235, MGL177, and MGL102 which are equivalent to *Bacillus* strain 101, 235, 177, and 102 respectively, as referred to in the application.

Any of these strains can be administered alone or in combination in the form of a feed composition (e.g., a complete feed comprising an animal feed blend) or drinking water for an animal. In one embodiment, multiple strains are administered in combination in a single composition. In another embodiment, multiple strains are administered in combination in separate compositions. In one illustrative embodiment, any of these strains is isolated from a grow finish pig.

As used herein "a strain having all of the identifying characteristics of" *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177 can be a mutant strain having all of the identifying characteristics of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177 (e.g., a DNA fingerprint based on DNA analysis that corresponds to the DNA fingerprint of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, enzyme activities that correspond to *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, antimicrobial activity that corresponds to *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, antibiotic sensitivity or tolerance profiles that correspond to *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or combinations of these identifying characteristics). In alternate embodiments, the mutation can be a natural mutation, or a genetically engineered mutation. In another embodiment, "a strain having all of the identifying characteristics of" *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, can be a strain, for example, produced by isolating one or more plasmids from *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, and introducing the one or more plasmids into another bacterium, such as another *Bacillus* strain, as long as the one or more plasmids contain DNA that provides the identifying characteristics of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177 (e.g., a DNA fingerprint based on DNA analysis that corresponds to the DNA fingerprint of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177).

The feed composition or drinking water comprising *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, may be administered to the animal for any time period that is effective to cause virus inhibition or control a detrimental effect of a virus. For example, in one embodiment the feed composition or drinking water may be provided to the animal daily. In an alternate embodiment, the feed composition or drinking water may be administered to the animal during lactation and/or during gestation. The time periods for administration of the feed composition or drinking water described above are non-limiting examples and it should be appreciated that any time period or administration schedule determined to be effective to cause virus inhibition or control a detrimental effect of a virus, or reduce or prevent symptoms of viral disease, or reduce the number of viruses in the animal, or combinations thereof, may be used.

In an additional embodiment of the invention, compositions comprising *Bacillus* strain A12, and/or *Bacillus* strain 54, and/or *Bacillus* strain 681, and/or *Bacillus* strain 721, and/or *Bacillus* strain 300, and/or *Bacillus* strain 86 are provided. In another embodiment of the invention, compositions comprising *Bacillus* strain 101, and/or *Bacillus* strain 102, and/or *Bacillus* strain 177, and/or *Bacillus* strain 235, and/or *Bacillus* strain 300, and/or *Bacillus* strain 86 are provided.

In one embodiment, a commercial package is provided comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

In another illustrative embodiment, a feed additive for an animal feed is provided comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

In another embodiment, an additive for the drinking water of an animal is provided comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

In another aspect, an animal feed composition is provided comprising *Bacillus* strain 300 (NRRL No. B-50943) or a strain having all of the identifying characteristics of *Bacillus* strain 300 (NRRL No. B-50943), *Bacillus* strain 86 (NRRL No. B-50944) or a strain having all of the identifying characteristics of *Bacillus* strain 86 (NRRL No. B-50944), *Bacillus* strain A12 (NRRL No. B67516) or a strain having all of the identifying characteristics of *Bacillus* strain A12 (NRRL No. B67516), *Bacillus* strain 54 (NRRL No. B67517) or a strain having all of the identifying characteristics of *Bacillus* strain 54 (NRRL No. B67517), *Bacillus* strain 681 (NRRL No. B67515) or a strain having all of the identifying characteristics of *Bacillus* strain 681 (NRRL No. B67515), and *Bacillus* strain 721 (NRRL No. B67514) or a strain having all of the identifying characteristics of *Bacillus* strain 721 (NRRL No. B67514).

In yet another embodiment, a commercial package is provided comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

In still another embodiment, a feed additive for an animal feed is provided comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

In another illustrative embodiment, an additive for the drinking water of an animal is provided comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

In another aspect, an animal feed composition is provided comprising *Bacillus* strain 300 (NRRL No. B-50943) or a strain having all of the identifying characteristics of *Bacillus* strain 300 (NRRL No. B-50943), *Bacillus* strain 86 or a strain having all of the identifying characteristics of *Bacillus* strain 86 (NRRL No. B-50944), *Bacillus* strain 101 (NRRL No. B-67218) or a strain having all of the identifying characteristics of *Bacillus* strain 101 (NRRL No. B-67218), *Bacillus* strain 235 (NRRL No. B-67219) or a strain having all of the identifying characteristics of *Bacillus* strain 235 (NRRL No. B-67219), *Bacillus* strain 102 (NRRL No. B-67276) or a strain having all of the identifying characteristics of *Bacillus* strain 102 (NRRL No. B-67276), and *Bacillus* strain 177 (NRRL No. B-67275) or a strain having all of the identifying characteristics of *Bacillus* strain 177 (NRRL No. B-67275).

In one embodiment, the feed additive for addition to an animal feed blend to produce a complete feed composition can be mixed with the animal feed blend, for example, with an automated micro-nutrient delivery system, or, for example, by hand-weighing and addition to achieve any of the doses of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, described herein, for administration to the animal in the form of a complete feed composition. The mixing can also be done by any other suitable method known in the art for combining direct-fed microbials with an animal feed blend to obtain a uniform mixture. In various embodiments, the mixing can be done for any suitable time period (e.g., about 1 to about 4 minutes). In the embodiments where *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, is in the form of an additive for the drinking water of the animal, the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, can be in the form of, for example, a powder, a liquid, or pellets, and can be mixed with the drinking water using any suitable method known in the art to achieve any of the doses of *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, described herein, for administration to the animal in the drinking water of the animal. *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, can also be fed directly to the animal orally (i.e., by oral insertion) in the form of a powder, a liquid, or a pellet.

In any of the composition embodiments described herein, the *Bacillus* strain *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, can cause an effect selected from the group consisting of causing virus inhibition in the animal or controlling a detrimental effect of a virus, including, but not limited to, reducing the number of viruses in the animal, controlling or reducing viral replication in the animal, preventing or reducing viral disease in the animal, or preventing or reducing any of the symptoms of viral disease in the animal, or a combination thereof. In another aspect, the virus inhibition or controlling the detrimental effect of the virus in the animal can comprise, for example, reducing or preventing enteric disease in the animal or reducing or preventing pneumonia in the animal. In other embodiments of the composition embodiments described herein, *E. coli* virulence genes can be reduced in the animal, or *Salmonella* disease can be reduced in the animal, for example, *Salmonella* disease caused by *Salmonella choleraesuis*, as a result of feeding the animal the *Bacillus* strain.

In one illustrative aspect, the feed additive, additive for the drinking water of the animal, or the feed composition can be in the form of a commercial package. In another illustrative embodiment, the feed additive or additive for the drinking water of the animal, or the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, in the commercial package can be in the form of a concentrate (e.g., about $1 \times 10^8$ to about $5 \times 10^9$ CFU/g) or a superconcentrate (e.g., about $1 \times 10^{10}$ to about $5 \times 10^{12}$ CFU/g). In another embodiment, the feed additive, feed composition, or additive for the drinking water of the animal, or the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics, in a composition in a commercial package, can be in a dry form (e.g., a powder), a pelleted form, a liquid form, in the form of a top-dressing, or in the form of a gel, or any other suitable form.

In yet another embodiment, the strains in the form of a commercial package can be, for example, in a dry form (e.g., a powder or freeze-dried form), in a pelleted form, or in a liquid form.

In another illustrative embodiment, the commercial package, feed additive, additive for the drinking water of the animal, or feed composition can further comprise a carrier for the *Bacillus* strain A12, and/or *Bacillus* strain 54, and/or *Bacillus* strain 681, and/or *Bacillus* strain 721, and/or *Bacillus* strain 300, and/or *Bacillus* strain 101, and/or *Bacillus* strain 235, and/or *Bacillus* strain 86, and/or *Bacillus* strain 102, and/or *Bacillus* strain 177, or strains with their identifying characteristics. The carrier can be selected from the group consisting of a bran, rice hulls, a salt, mineral oil, a dextrin (e.g., maltodextrin), whey, sugar, sucrose, limestone, yeast culture, dried starch, sodium silico aluminate, silicon dioxide, polypropylene glycol, polysorbate 80, vegetable oil, and combinations thereof. In another embodiment, the carrier can be any suitable carrier known in the art for a direct-fed microbial. In another embodiment, the commercial package, feed additive, additive for the drinking water of the animal, or feed composition can further comprise a binder such as clay, yeast cell wall components, aluminum silicate (HSCAS), glucan, or other known binders. In another embodiment, the commercial package, feed additive, additive for the drinking water of the animal, or feed composition can further comprise inorganic/organic binders, essential oils, and/or organic acids.

In yet other embodiments, the commercial package, feed additive, additive for the drinking water of the animal, or feed composition comprising *Bacillus* strain A12, and/or Bacillus strain 54, and/or Bacillus strain 681, and/or Bacillus strain 721, and/or Bacillus strain 300, and/or Bacillus strain 101, and/or Bacillus strain 235, and/or Bacillus strain 86, and/or Bacillus strain 102, and/or Bacillus strain 177, or strains with their identifying characteristics is in a container for commercial use. In various embodiments the container can be, for example, a bag (e.g., a 20-pound bag, a 50-pound bag, a 2-ounce bag, a 1-pound bag, or a 1-kilogram bag), a pouch, a drum, a bottle, or a box. In illustrative aspects, the container for the commercial package, feed additive, additive for the drinking water of the animal, or feed composition comprising Bacillus strain A12, and/or Bacillus strain 54, and/or Bacillus strain 681, and/or Bacillus strain 721, and/or Bacillus strain 300, and/or Bacillus strain 101, and/or Bacillus strain 235, and/or Bacillus strain 86, and/or Bacillus strain 102, and/or Bacillus strain 177, or strains with their identifying characteristics, can comprise plastic, metal, foil, paper, fiber, or cardboard (e.g., a plastic pail, a paper bag, a foil bag, a fiber drum, etc.). The commercial package, feed additive, additive for the drinking water of the animal, or feed composition can further comprise instructions for use of one or more of the Bacillus strains.

The following EXAMPLES provide various additional illustrative aspects of the invention described herein and are not intended to be limiting in any way.

EXAMPLES

Example 1

Rotavirus Analysis in Commercial Swine Facilities

To determine the impact Provent ECL (comprised of Bacillus strains 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275)) has on Rotavirus gene presence and associated enteric disease, rectal swabs from sows and their progeny were taken in five different commercial sow units and meta-analyzed to determine gene differences before and after Provent ECL use. RNA and subsequent cDNA was acquired from all swabs, and qPCR was utilized to determine gene quantities of Rotavirus A and Rotavirus C. Understanding that Rotavirus and E. coli may synergistically work together to cause more severe disease, E. coli virulence genes were also quantified to determine if they were impacted by Provent ECL use.

Example 2

S. Choleraesuis/PRRSV Challenge Study

A controlled study was conducted to monitor the effects of Provent ECL (comprised of Bacillus strains 300 (NRRL No. B-50943), 86 (NRRL No. B-50944), A12 (NRRL No. B67516), 54 (NRRL No. B67517), 681 (NRRL No. B67515), and 721 (NRRL No. B67514)) on animals dually challenged with S. choleraesuis var Kunzendorf and PRRSV (porcine reproductive and respiratory syndrome virus) NADC20. Animals 21 days of age were transitioned to a standard balanced swine nursery diet and fed for the duration of the study either with or without Provent ECL supplementation. Two weeks after weaning, animals were challenged orally with S. choleraesuis, and three days later received an additional intranasal challenge of PRRSV. Animals were monitored for 17 days following the bacterial challenge for clinical signs and viremia. At the end of the observation period, the animals were euthanized, and a full necropsy was performed and their bodies scored for the presence of pathological lesions. The presence of PRRSV and S. choleraesuis in selected organs and tissues was determined using quantitative methods. Cytokine concentrations were measured in clinical samples (bronchoalveolar lavage) obtained at the time of necropsy from the subjects of the indicated treatment groups. The cytokine levels were measured using a porcine cytokine bead array and reported adjusted to picograms of cytokine per 1 mg/ml of protein in the sample.

Example 3

Figure 2:
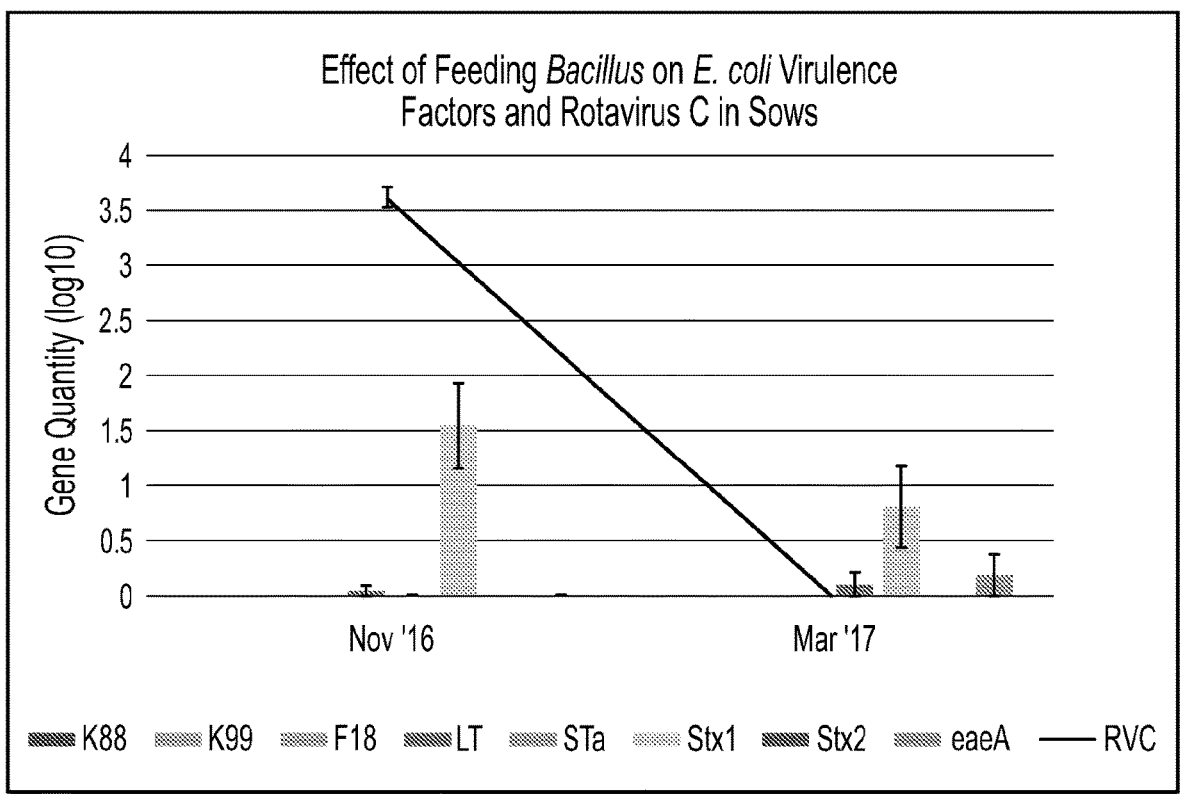
FIG. 2 is a graph showing a gene quantity comparison between two sampling time points in sow unit A. The bars correspond to the legend left to right in each dated group.
Figure 3:
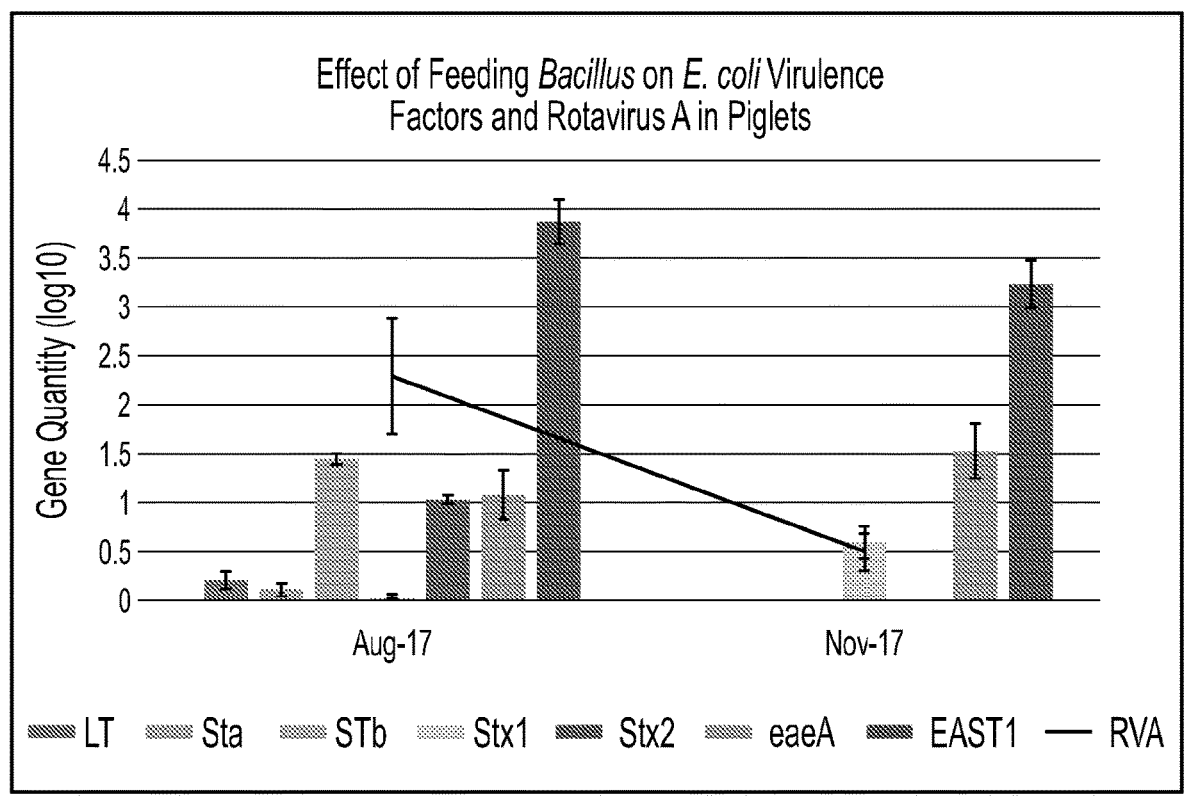
FIG. 3 is a graph showing a gene quantity comparison between two sampling time points in sow unit B. The bars correspond to the legend left to right in each dated group.
Figure 4:
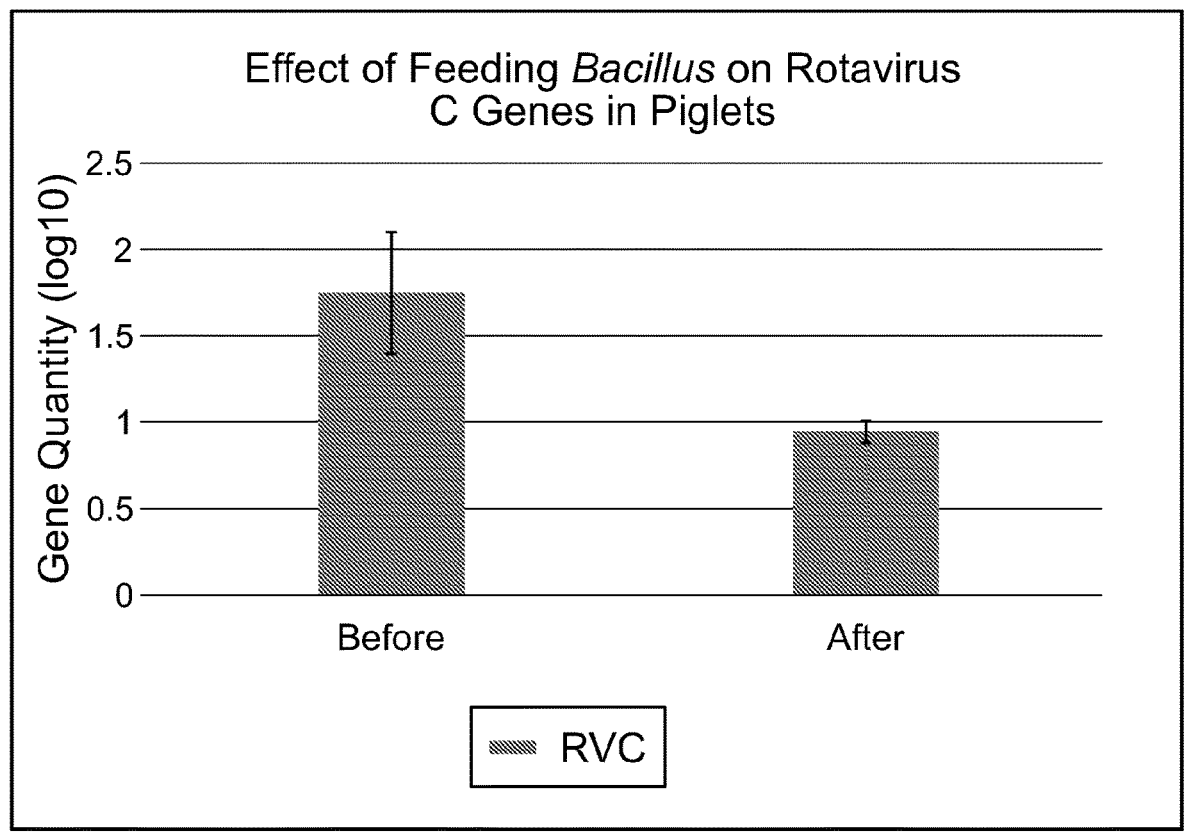
FIG. 4 is a graph showing a gene quantity meta-analysis studying piglets from five different sow farms before and after Provent ECL use.

Rotavirus Analysis in Commercial Swine Facilities qPCR and subsequent meta-analysis determined that Rotavirus C quantities decreased significantly ($P<0.05$) in piglets whose maternal sow was fed Provent ECL (FIG. 4). Sow unit A showed a significant reduction of Rotavirus C in both piglets and sows ($P<0.05$) in addition to reducing multiple E. coli virulence factors (FIGS. 1-2). Rotavirus influenced pre-wean mortality was also reduced in sow unit A by 19% after Provent ECL use (FIG. 2). Piglets from sow unit B harbored lower Rotavirus A genes ($P=0.051$) in addition to lower quantities of numerous E. coli virulence genes after Provent ECL was implemented (FIG. 3). Sow unit B and a sister sow site within the same pod had both been affected by PRRSV within the last 12 months. During this evaluation period, sow site B consuming Provent ECL did not break with PRRSV while the sister site not consuming Provent ECL re-broke with PRRSV.

Example 4

S. Choleraesuis/PRRSV Challenge Study

Feeding animals Provent ECL for 3 weeks prior to S. choleraesuis and PRRSV exposure reduced the severity of disease as indicated by a reduction in the extent of gross lung pathology and fibrinous peritonitis. In addition, Provent ECL fed animals had reduced spread of S. choleraesuis from the gastrointestinal tract into the respiratory tract during the co-infection with PRRS virus (Table 1). The type of pneumonia exhibited by several of the dually challenged pigs was characterized not only by the presence of interstitial pneumonia involving>50% of the lung, but also by the presence of discrete areas of lung consolidation which are characteristic of bronchopneumonia. Severity of the bronchopneumonia resulting from the dual bacterial/viral co-infection was reduced by 32% in animals fed Provent ECL (Table 1).

TABLE 1

Pathological and microbiological findings observed in the challenge experiment.

| | Strict control Group 1 (n = 4) Pen 2 | Salmonella and PRRSV challenge Group 4 (n = 11) Pen 8 | Fed ECL2-Salmonella and PRRSV Challenge Group 5 (n = 10) Pen 7 |
|---|---|---|---|
| % Pigs with Salmonella isolated from either the lung or bronchial lymph node | 0 | 91 (10 of 11) | 60 (6 of 10) |
| % of pigs with >10 ml of ascites | 0 | 82 (9 of 11) | 50 (5 of 10) |
| Extent of gross lung pathology (% lung involvement ± SE) | 0 | 82.5 ± 2 | 52.7 ± 6 |

TABLE 1-continued

Pathological and microbiological findings observed in the challenge experiment.

|  | Strict control Group 1 (n = 4) Pen 2 | Salmonella and PRRSV challenge Group 4 (n = 11) Pen 8 | Fed ECL2-Salmonella and PRRSV Challenge Group 5 (n = 10) Pen 7 |
|---|---|---|---|
| % of pigs with bronchopneumonia | 0 | 82 (9 of 11) | 50 (5 of 10) |

Results obtained from BAL and whole blood samples suggest that animals fed Provent ECL had higher concentrations of bacterial and viral pathogen recognition receptors as well as in increase in anti-inflammatory cytokines (FIGS. 5A-5B and 6A-6B). These results provide evidence for the immunological modulation capabilities Provent ECL possesses and helps to explain the reduction in symptoms seen within treated animals.

Figure 7:
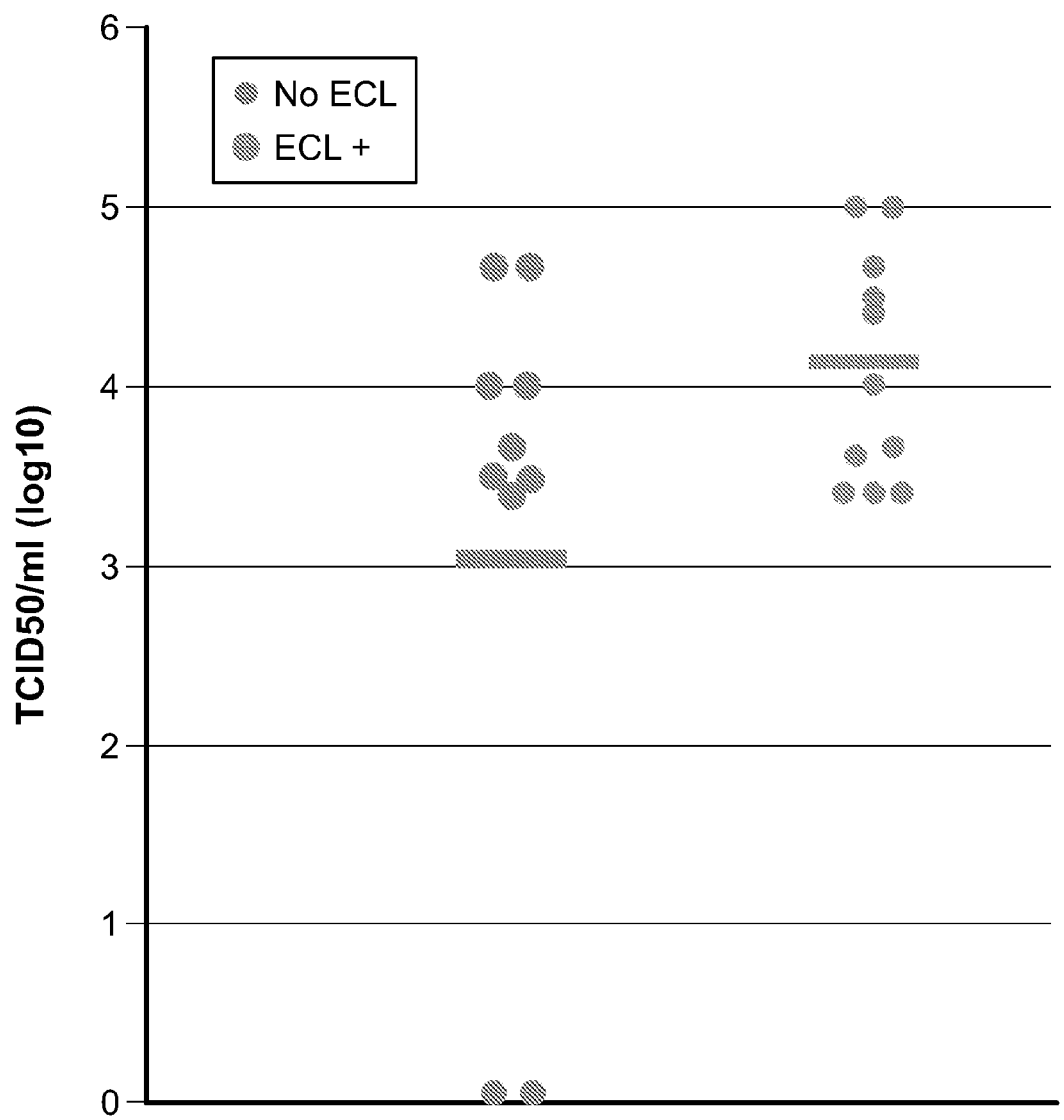
FIG. 7 is a graph showing viremia at the time of necropsy. Horizontal bars indicate the mean level of viremia of the group. The difference in the means of the two groups was statistically significant (p<0.05). The dots in the left column are ECL+ and the dots in the right column are No ECL.
Figure 8:
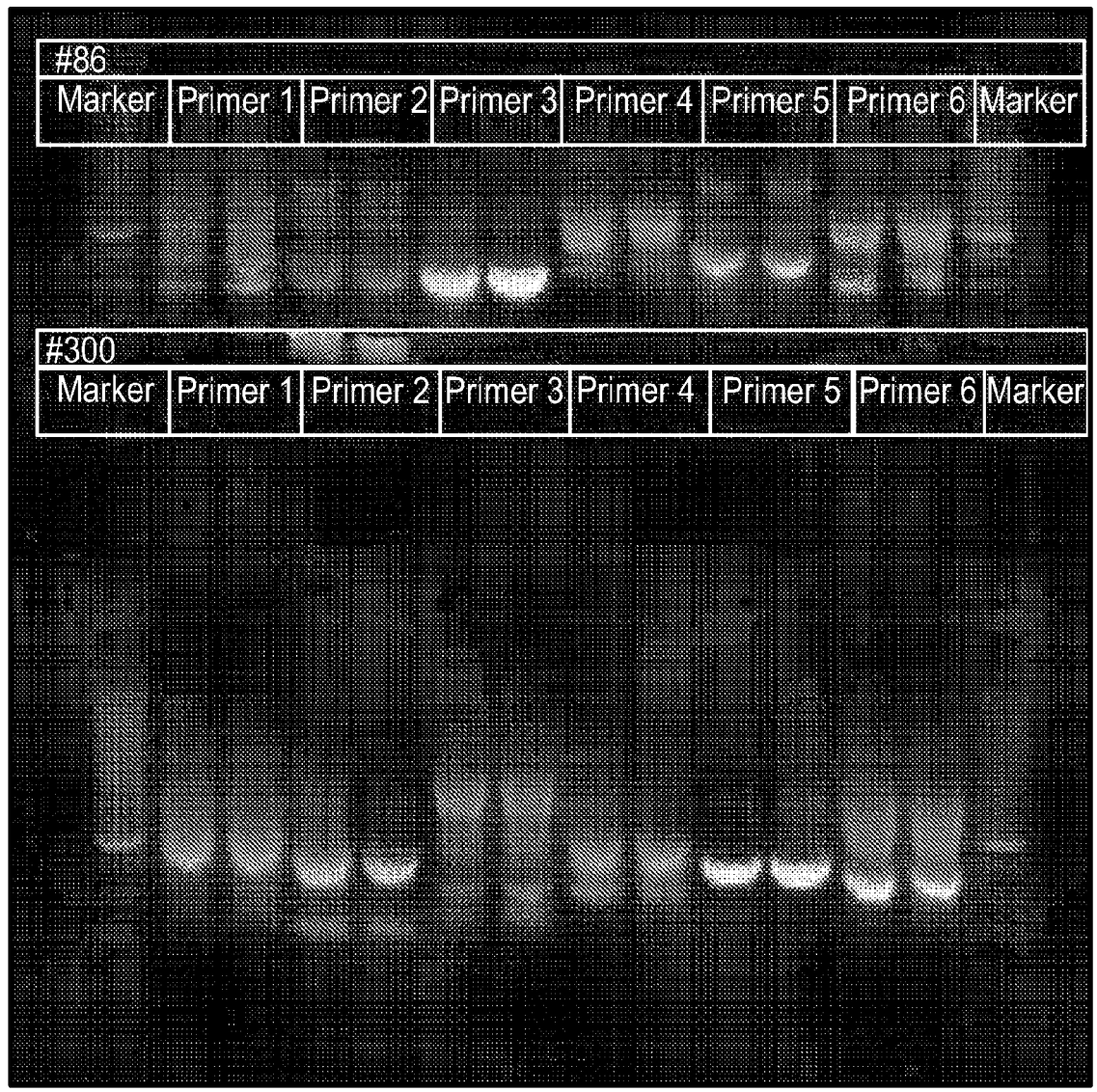
FIG. 8 shows a photograph of a gel displaying RAPD PCR profiles for *Bacillus* strains 86 and 300. Strain 86 has the top profile and strain 300 has the bottom profile.
Figure 9:
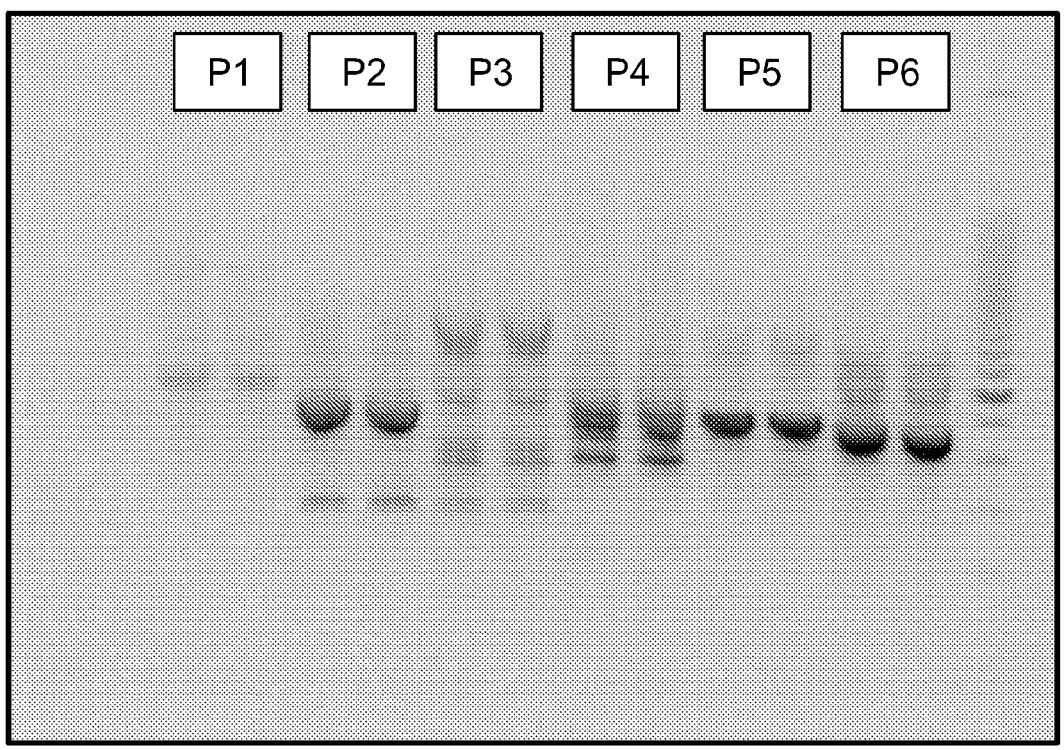
FIG. 9 shows a photograph of a gel displaying a RAPD PCR profile for *Bacillus* strain 101.
Figure 10:
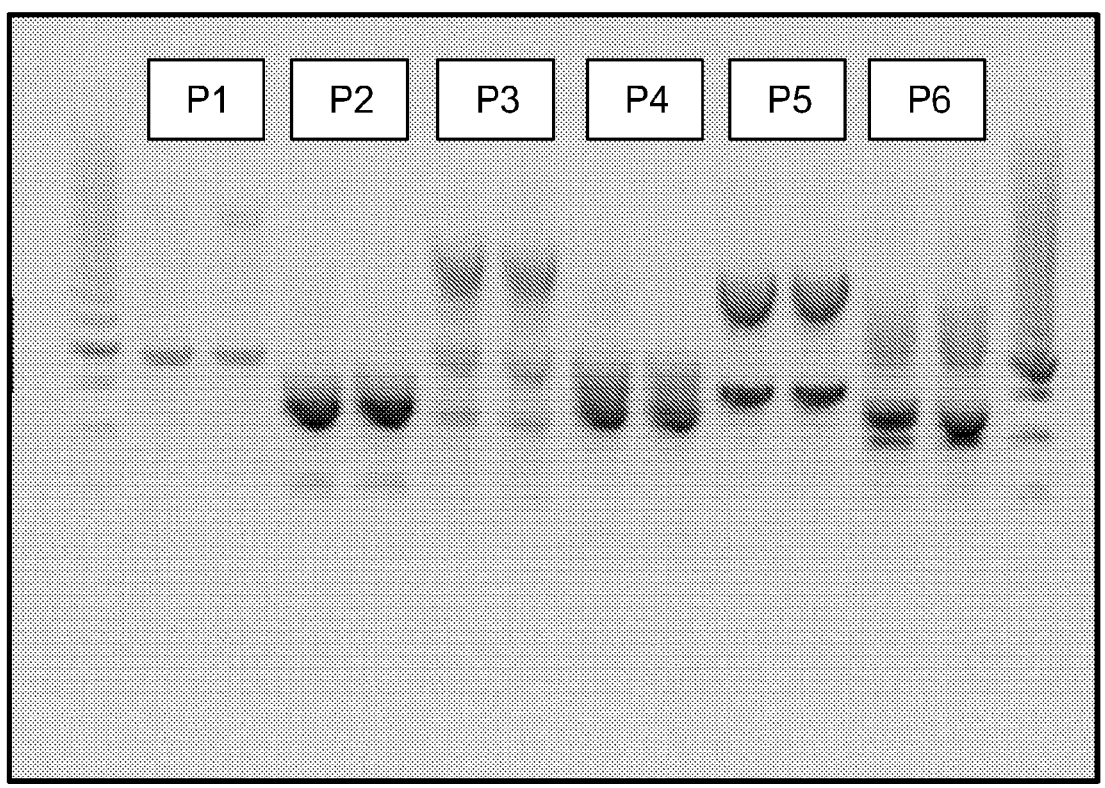
FIG. 10 shows a photograph of a gel displaying a RAPD PCR profile for *Bacillus* strain 235.
Figure 11:
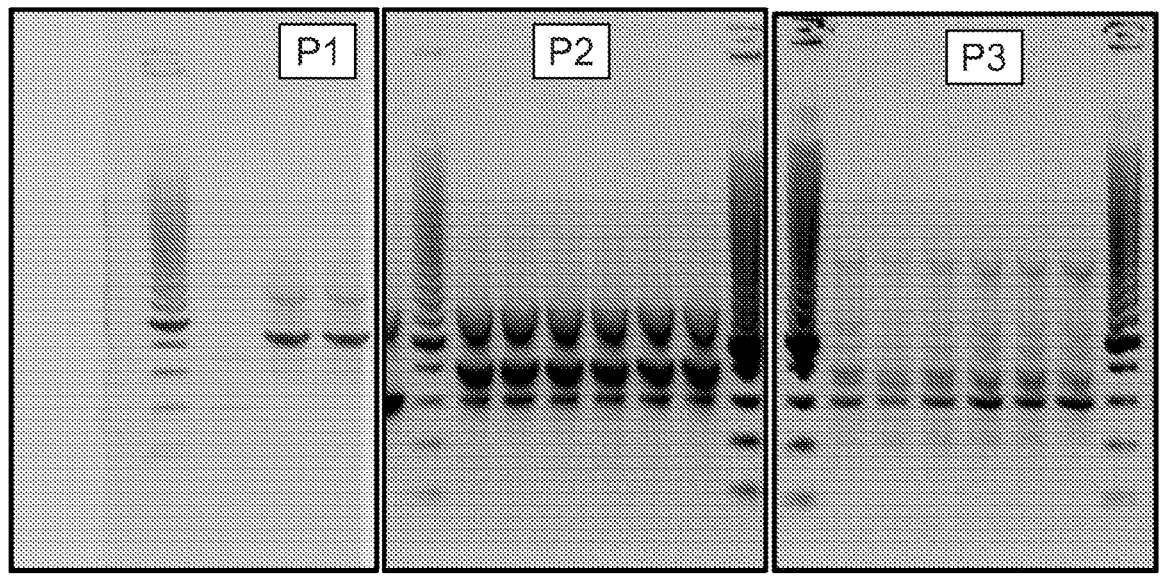
FIG. 11 shows a photograph of a gel displaying a RAPD PCR profile for *Bacillus* strain 102.
Figure 12:
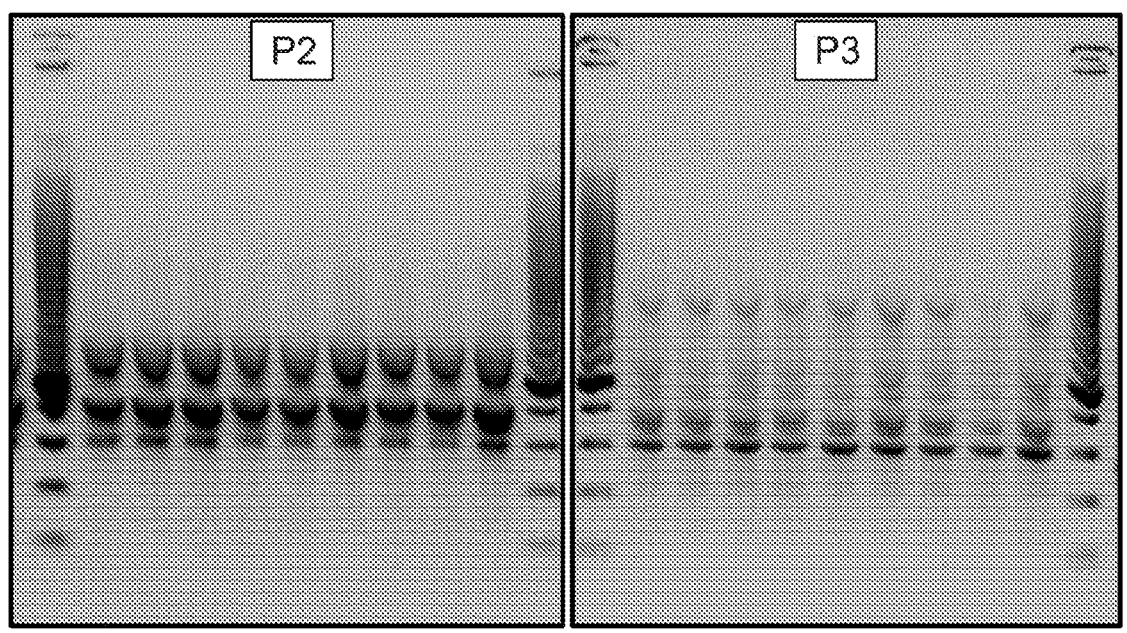
FIG. 12 shows a photograph of a gel displaying a RAPD PCR profile for *Bacillus* strain 177.
Figure 13A:
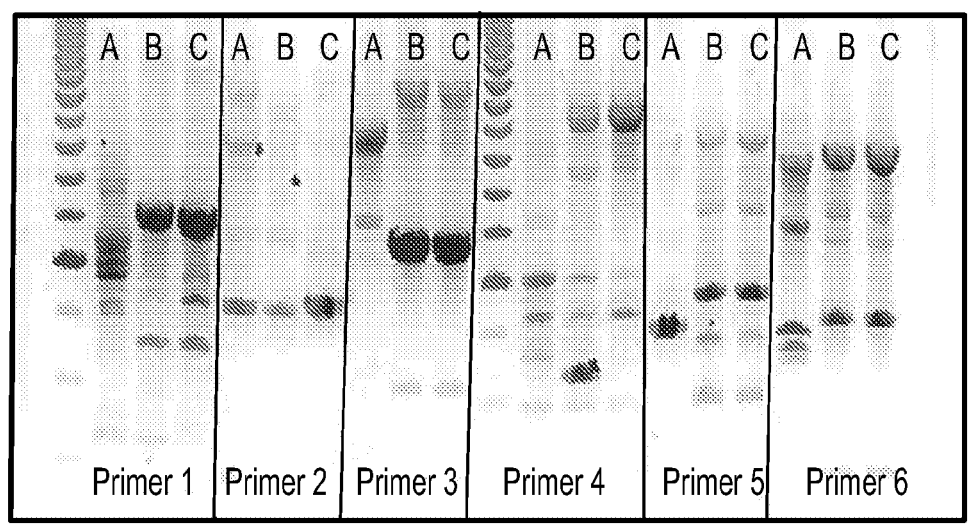
FIG. 13A shows a photograph of a gel displaying a RAPD PCR profile for *Bacillus* strains 681 and 721.
Figure 13B:
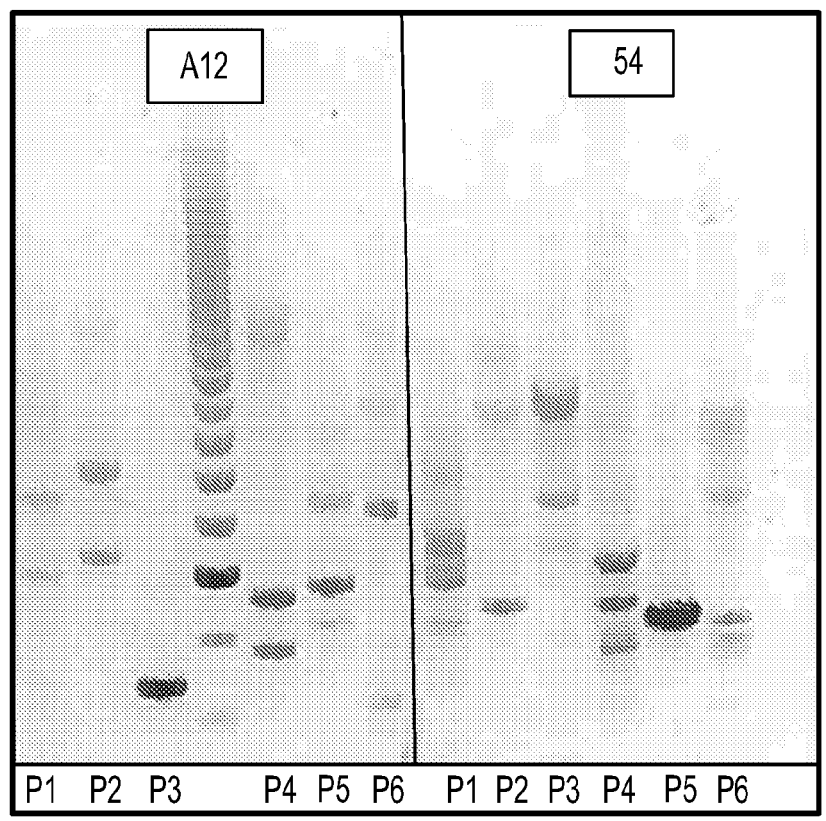
FIG. 13B shows a photograph of a gel displaying a RAPD PCR profile for *Bacillus* strains A12 and 54.

Most notably, the inclusion of Provent ECL in swine diets for 3 weeks before exposure to *S. choleraesuis* and PRRS virus reduced the level of viremia by 10-fold (P<0.05) with two animals having no detectable levels of virus in their serum (FIG. 7).

Example 5

Discussion

Based on statistical meta-analysis, Rotavirus genes were reduced in commercial sow unit piglets whose maternal sows were fed Provent ECL. In a separate controlled study, Provent ECL reduced the incidence and severity of disease associated with S. cholerasuis and PRRSV coinfection, and significantly reduced the quantity (TCID50/mL) of PRRS virus in animals fed Provent ECL compared to the control population. These results provide empirical evidence that *Bacillus* contributes to the protection and reduction of PRRSV and Rotavirus associated viremia in addition to reducing viral genes within swine populations. *Bacillus* strains comprised in Provent ECL, namely *Bacillus* strains 300 (NRRL No. B-50943), 101 (NRRL No. B-67218), 235 (NRRL No. B-67219), 86 (NRRL No. B-50944), 102 (NRRL No. B-67276), and 177 (NRRL No. B-67275), A12 (NRRL No. B67516), 54 (NRRL No. B67517), 681 (NRRL No. B67515), and 721 (NRRL No. B67514) assist in the prevention and reduction of viral disease through direct or indirect means.

Example 6

DNA Fingerprints

DNA fingerprints for *Bacillus* strains 300, 101, 235, 86, 102, 177, A12, 54, 681, and 721 of the present application were obtained using the READY-TO-GO™ RAPD Analysis Beads kit (GE Healthcare, Chicago, IL), designed as premixed, pre-dispensed reactions for performing RAPD analysis. DNA was extracted using the QIAGEN® Tissue and Blood single column kit (QIAGEN®, Venlo, The Netherlands).

Example 7

Experimental Design of ECL Treatment and PRRSV-*Salmonella Choleraesuis* Co-Infection Forty-eight, 3-week-old pigs free of PRRSV, PCV2, *Mycoplasma hyopneumoniae*, and *Salmonella choleraesuis* were randomly assigned to five treatment groups listed in Table 1. Four pigs were allocated to group 1, and eleven pigs were allocated to each of the other four groups.

TABLE 1

Experimental design of ECL treatment and PRRSV-*Salmonella choleraesuis* co-infection

| Group | | Pigs per | | Treatment day | | | |
|---|---|---|---|---|---|---|---|
| No. | Pen | group | Treatment Designation | −21 | 0 | 3 | 8/9 |
| 1 | 2 | 4 | Control (No DFM-no challenge) | — | Mock | Mock | Euthanasia |
| 2 | 4 | 11 | *Salmonella* challenge control | — | *S. choleraesuis* | Mock | Euthanasia |
| 3 | 3 | 11 | DFM and *S. choleraesuis* challenge | Start ECL | *S. choleraesuis* | Mock | Euthanasia |
| 4 | 8 | 11 | PRRSV/*Salmonella* challenge control | — | *S. choleraesuis* | PRRSV | Euthanasia |
| 5 | 7 | 11 | DFM and PRRSV/*S. choleraesuis* challenge | Start ECL | *S. choleraesuis* | PRRSV | Euthanasia |

After euthanasia, a full necropsy was performed and scored for the presence of pathological lesions. The presence of *S. choleraesuis* in selected organs and tissues was determined using quantitative methods. Blood and gastrointestinal tract swabs were obtained and tested for various immune markers and enteric virulence genes.

Example 8

Pathological and Microbiological Findings Observed in the Main Experiment

Pathological and microbiological findings observed in the main experiment are shown in Table 2.

TABLE 2

| | Strict control Group 1 (n = 4) Pen 2 | *Salmonella* challenge only Group 2 (n = 11) Pen 4 | Fed ECL2-*Salmonella* challenge only Group 3 (n = 11) Pen 3 | *Salmonella* and PRRSV challenge Group 4 (n = 11) Pen 8 | Fed ECL2-*Salmonella* and PRRSV Challenge Group 5 (n = 10) Pen 7 |
|---|---|---|---|---|---|
| % Pigs with *Salmonella* isolated from either the lung or bronchial lymph node | 0 | 36 (4 of 11) | 36 (4 of 11) | 91 (10 of 11) | 60 (5 of 10) |
| % of pigs with >10 ml of ascites | 0 | 63 (7 of 11) | 27 (3 of 11) | 82 (9 of 11) | 50 (5 of 10) |
| Extent of gross lung pathology (% lung involvement ± SE) | 0 | 49.4 ± 6 | 23.6 ± 4 | 82.5 ± 2 | 52.7 ± 6 |

Pathological and microbiological findings observed in the main experiment.

Figure 5A:
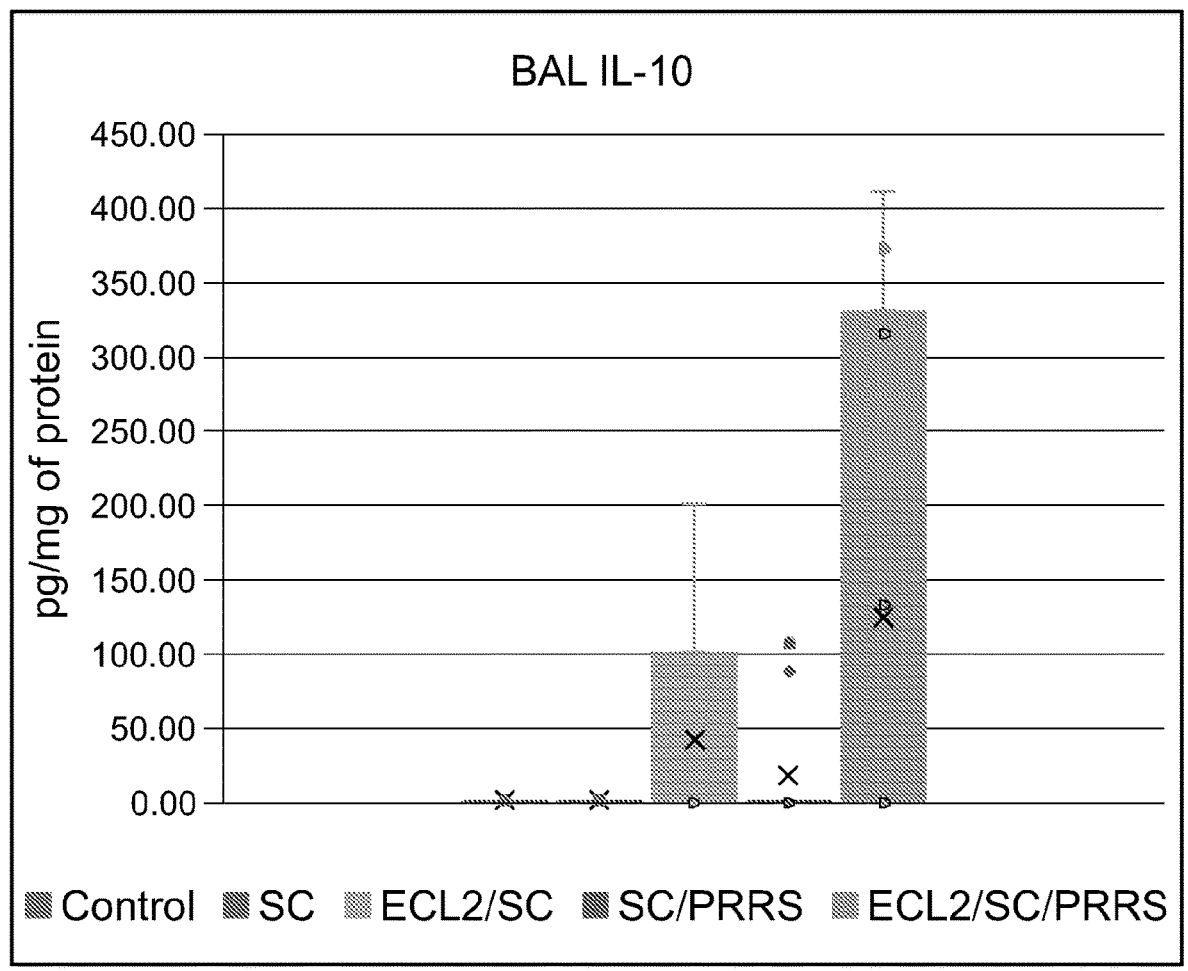
FIGS. 5A-5B are graphs showing levels of immune regulatory cytokines (IL-10 and IL-4) present in the bronchoalveolar lavage of pigs inoculated 8 days earlier with *S. choleraesuis* followed three days later by an intranasal inoculation with PRRS virus. The bars correspond to the legend left to right.
Figure 5B:
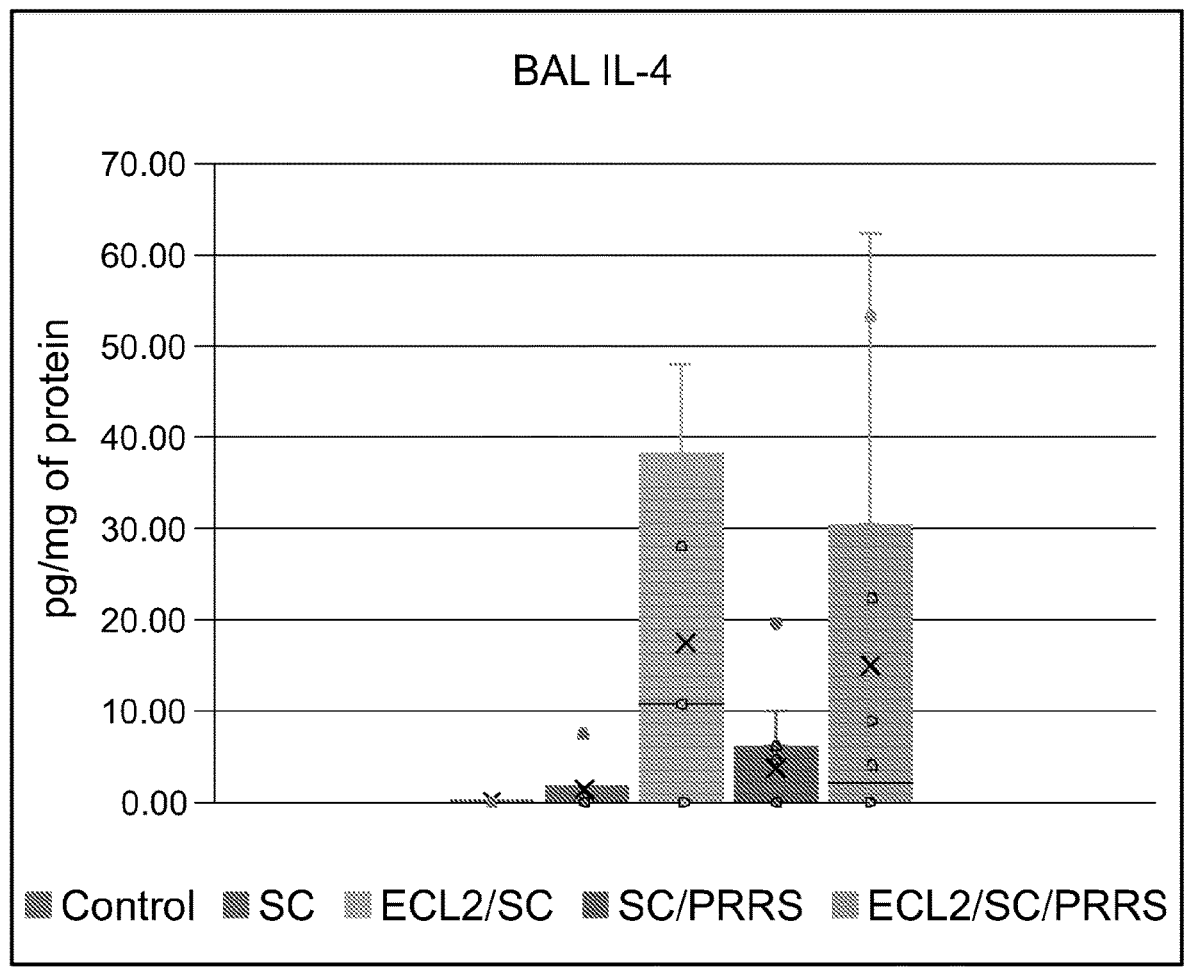
Figure 6A:
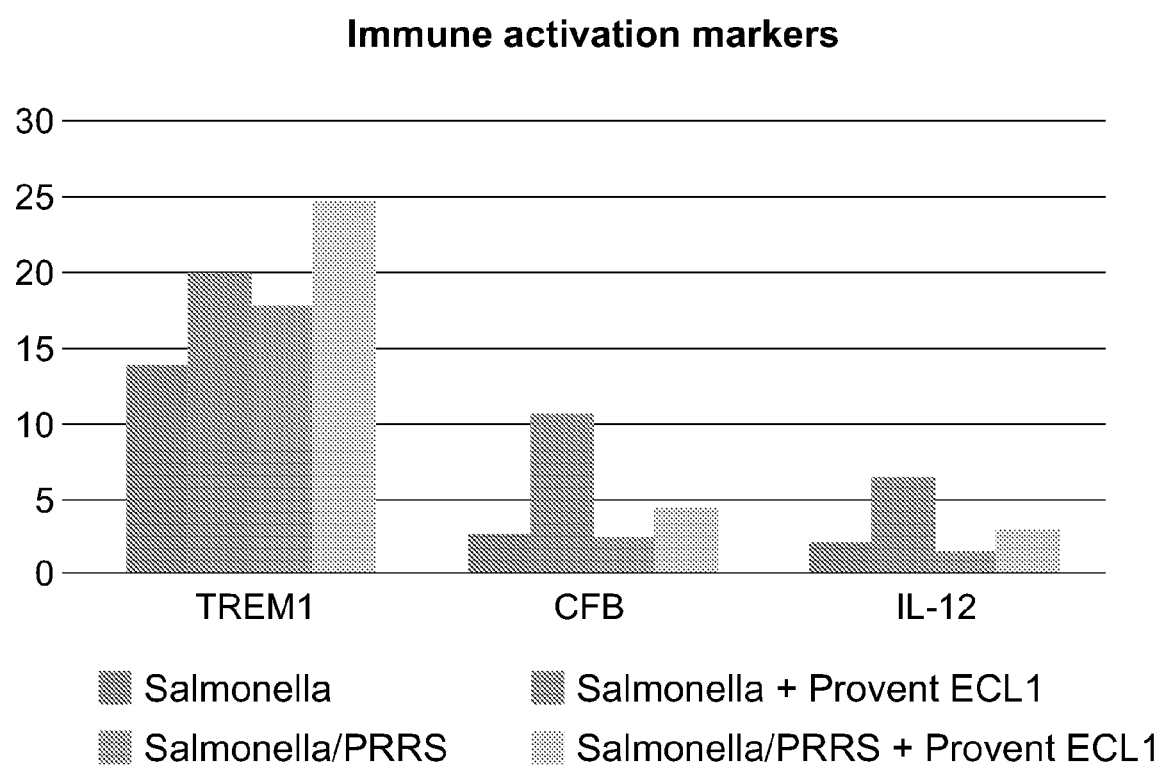
FIGS. 6A-6B are graphs showing expression of immune markers (TREM1, CFB, IL-12, NOD1, NOD2, and DHX58) obtained from whole blood samples; for all markers there is significant effect of Provent ECL (p<0.05, two-way ANOVA). The bars for each group from left to right correspond to "*Salmonella*", "*Salmonella*+Provent ECL1", "*Salmonella* PRRS", and "*Salmonella*/PRRS+Provent ECL1".
Figure 6B:
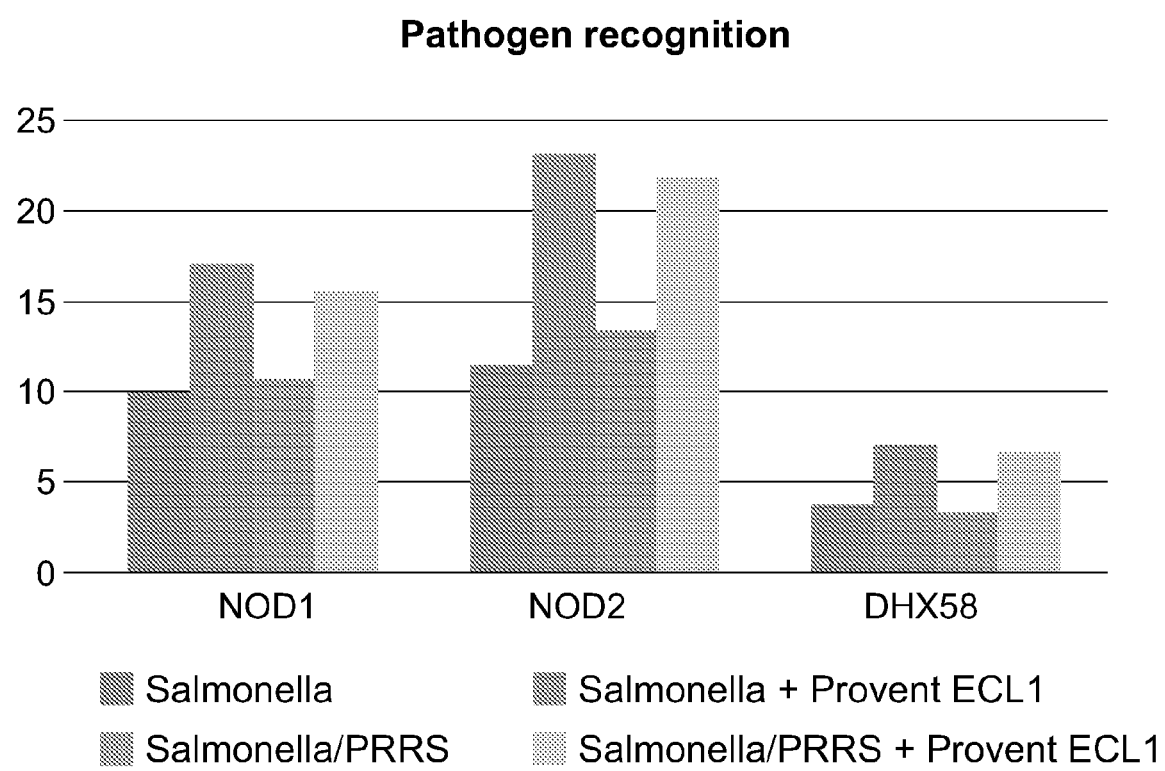
Figure 14:
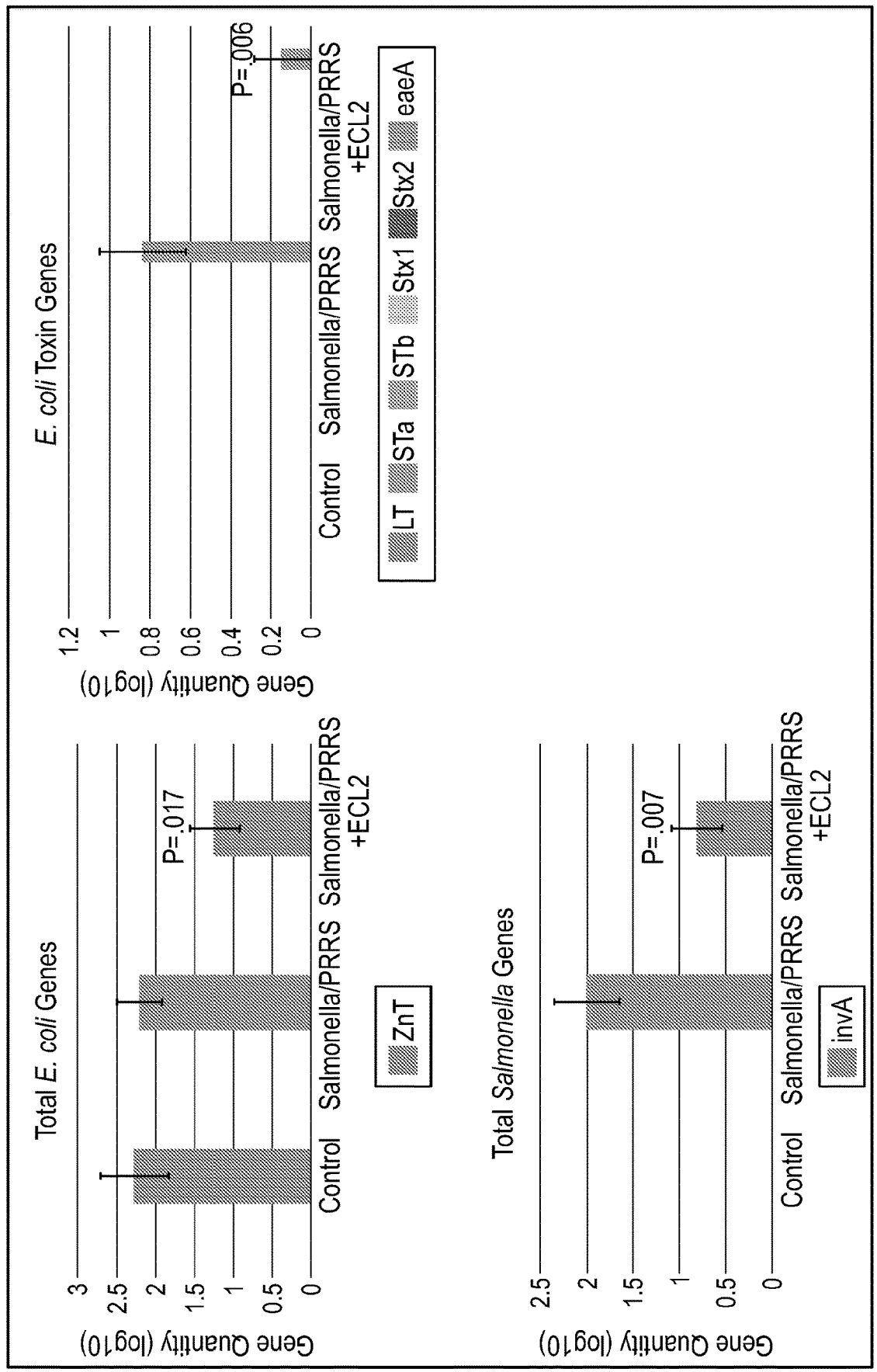
FIG. 14 shows log 10 quantities of *E. coli* and *Salmonella* virulence genes obtained from gastrointestinal samples from animals belonging to different treatment groups. P values obtained via one way t-test comparing *Salmonella*/PRRS and *Salmonella*/PRRS+DFM treatments.

The results indicated that the inclusion of *Bacillus* strains A12, 54, 681, and 721 in the diet of swine for 3 weeks before exposure to *S. choleraesuis* reduced the severity of the respiratory disease as indicated by a reduction in the extent of gross lung pathology and fibrinous peritonitis. This effect was observed in animals inoculated with either *Salmonella* alone or both *Salmonella* and PRRSV. Both *Salmonella* and *E. coli* virulence genes were detected at significantly lower quantities in the gastrointestinal tract (GIT) of animals fed these strains (FIG. 14). In addition, they also reduced the spread of bacteria from the GIT into the respiratory tract during a co-infection with PRRS virus Immune activation markers were significantly different in animals fed the combination of A12 (NRRL No. B67516), 54 (NRRL No. B67517), 681 (NRRL No. B67515), and 721 (NRRL No. B67514) (FIGS. 5A and B and FIGS. 6A and B).

What is claimed is:

1. A method of feeding an animal to reduce the risk of viral infection, the method comprising the step of administering to the animal a feed composition or drinking water comprising an effective amount of an additive comprising theisolated *Bacillus* strain A12, assigned accession no. NRRL B-67516, and
one or more isolated *Bacillus* strains selected from the group consisting of *Bacillus* strain 54, assigned accession no. NRRL B-67517, *Bacillus* strain 681, assigned accession no. NRRL B-67515, *Bacillus* strain 721, assigned accession no. NRRL B-67514, *Bacillus* strain 300, assigned accession no. NRRL B-50943, *Bacillus* strain 101, assigned accession no. NRRL B-67218, *Bacillus* strain 235, assigned accession no. NRRL B-67219, *Bacillus* strain 86, assigned accession no. NRRL B-50944-*Bacillus* strain 102, assigned accession no. NRRL B-67276 and *Bacillus* strain 177, assigned accession no. NRRL B-67275, and combinations thereof,
wherein administering the *Bacillus* strains causes virus inhibition in the animal.

2. The method of claim 1 wherein the animal is selected from the group consisting of a poultry species, a porcine species, a caprine species, a bovine species, an ovine species, an equine species, and a companion animal.

3. The method of claim 2 wherein the animal is a porcine species and the porcine species is selected from the group consisting of a grow finish pig, a nursery pig, a sow, and a breeding stock pig.

4. The method of claim 1 wherein the virus is a Rotavirus.

5. The method claim 4 wherein the Rotavirus is Rotavirus A or Rotavirus C.

6. The method of claim 1 wherein the virus is a respiratory virus.

7. The method of claim 6 wherein the respiratory virus is a porcine reproductive and respiratory syndrome virus.

8. The method of claim 1 further comprising the step of administering an antibiotic to the animal.

9. The method of claim 1 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

10. The method of claim 9 wherein the enzyme is an NSPase or a phytase.

11. The method of claim 1 wherein said additive further comprises an isolated *Bacillus* strain selected from the group consisting of *Bacillus* strain 300, assigned accession no. NRRL B-50943, *Bacillus* strain 86, assigned accession no. NRRL B-50944, *Bacillus* strain 54, assigned accession no. NRRL B-67517, *Bacillus* strain 681, assigned accession no. NRRL B-67515, and *Bacillus* strain 721, assigned accession no. NRRL B-67514.

* * * * *